(12) United States Patent
Gusenoff et al.

(10) Patent No.: US 11,918,793 B2
(45) Date of Patent: Mar. 5, 2024

(54) METHODS AND DEVICES FOR USE IN TREATMENT OF PLANTAR FASCIITIS AND FAT GRAFTING

(71) Applicant: University of Pittsburgh—Of the Commonwealth System of Higher Education, Pittsburgh, PA (US)

(72) Inventors: Jeffrey A. Gusenoff, Pittsburgh, PA (US); Beth R. Gusenoff, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1024 days.

(21) Appl. No.: 16/642,568

(22) PCT Filed: Aug. 28, 2018

(86) PCT No.: PCT/US2018/048278
§ 371 (c)(1),
(2) Date: Feb. 27, 2020

(87) PCT Pub. No.: WO2019/046256
PCT Pub. Date: Mar. 7, 2019

(65) Prior Publication Data
US 2020/0188602 A1 Jun. 18, 2020

Related U.S. Application Data

(60) Provisional application No. 62/550,966, filed on Aug. 28, 2017.

(51) Int. Cl.
*A61M 5/315* (2006.01)

(52) U.S. Cl.
CPC .... *A61M 5/31583* (2013.01); *A61M 5/31526* (2013.01); *A61M 5/31528* (2013.01);
(Continued)

(58) Field of Classification Search
CPC .......... A61M 5/31583; A61M 5/31526; A61M 5/31528; A61M 2205/08; A61M 2205/09; A61M 2210/086
See application file for complete search history.

(56) References Cited

U.S. PATENT DOCUMENTS 5,429,117 A   7/1995  McNamara et al.
5,786,207 A * 7/1998  Katz .................... C12M 45/05
                                                        435/308.1
(Continued)

FOREIGN PATENT DOCUMENTS

WO   2010148008 A1  12/2010
WO   2018111550 A1   6/2018

OTHER PUBLICATIONS

"P2S Syringe 'Push to Spin' Syringe for Fat Transfer", CTSI ProtoHype Competition, Apr. 2016, https://www.youtube.com/watch?v=CAGG9MJGOjA (PowerPoint slides submitted).
(Continued)

*Primary Examiner* — Nathan R Price
*Assistant Examiner* — Mark A Igel
(74) *Attorney, Agent, or Firm* — The Webb Law Firm

(57) ABSTRACT

Provided herein are devices useful in processing fat for fat grafting and for delivering fat tissue grafts to a patient. Also provided are devices and methods for fat grafting and for treatment of plantar fasciitis.

23 Claims, 17 Drawing Sheets

(52) U.S. Cl.
CPC ..... *A61M 2202/08* (2013.01); *A61M 2202/09* (2013.01); *A61M 2210/086* (2013.01)

(56) References Cited

U.S. PATENT DOCUMENTS

| | | | |
|---|---|---|---|
| 7,111,546 B2* | 9/2006 | Siegel | A47J 43/24 34/194 |
| 8,540,078 B2* | 9/2013 | Leach | B04B 3/00 422/535 |
| 9,581,942 B1* | 2/2017 | Shippert | G03G 15/20 |
| 2006/0213374 A1* | 9/2006 | Shippert | A61M 1/774 99/472 |
| 2007/0100277 A1* | 5/2007 | Shippert | A61M 1/00 604/27 |
| 2008/0171951 A1 | 7/2008 | Fell | |
| 2012/0232452 A1 | 9/2012 | Bushby | |
| 2013/0030322 A1* | 1/2013 | Levine | A61B 10/0283 600/566 |
| 2013/0158515 A1 | 6/2013 | Austen, Jr. | |
| 2014/0052040 A1 | 2/2014 | Coates et al. | |
| 2014/0066847 A1 | 3/2014 | Lalwani | |
| 2015/0352266 A1* | 12/2015 | Gourlay | A61M 1/67 604/542 |
| 2017/0113005 A1 | 4/2017 | Lindner et al. | |
| 2017/0224935 A1* | 8/2017 | Hoffmann | A61M 5/3202 |
| 2019/0328977 A1* | 10/2019 | Kirn | A61M 5/1782 |

OTHER PUBLICATIONS

Hovius et al., "Extensive Percutaneous Aponeurotomy and Lipografting: A New Treatment for Dupuytren Disease", Plast. Reconstr. Surg., 2011, pp. 221-228, vol. 128.
Hovius et al., "Percutaneous aponeurotomy and lipofilling (PALF): a regenerative approach to Dupuytren contracture", Clin. Plast. Surg., 2015, pp. 375-381, vol. 42.
Khouri et al., "Percutaneous Aponeurotomy and Lipofilling: A Regenerative Alternative to Flap Reconstruction?", Plast. Reconstr. Surg., 2013, pp. 1280-1290, vol. 132.
Pain Research Challenge, 2016, https://www.youtube.com/playlist?list=PLHW2InxpITOpbqoTHia7FkvB5SaMrQW1u (PowerPoint slides submitted).
Yanbin et al., "Treatment of Chronic Plantar Fasciitis with Percutaneous Latticed Plantar Fasciotomy", Journal of Foot & Ankle Surgery, 2015, pp. 856-859, vol. 54.

* cited by examiner

METHODS AND DEVICES FOR USE IN TREATMENT OF PLANTAR FASCIITIS AND FAT GRAFTING

CROSS REFERENCE TO RELATED APPLICATIONS

This application is the U.S. national phase of International Application No. PCT/US2018/048278 filed Aug. 28, 2018, and claims the benefit of U.S. Provisional Patent Application No. 62/550,966, filed Aug. 28, 2017, each of which is incorporated herein by reference in their entirety.

The plantar fascia is a fibrous band that originates at the heel bone and inserts into the heads of the metatarsal bones at the bottom of one's foot. Acute plantar fasciitis develops as a result of an excessive amount of traction on the ligament during stance and ambulation. Classic symptoms of plantar fasciitis include pain at the heel when first rising from a resting position. In acute plantar fasciitis the pain will improve on ambulation as the plantar fascia warms up and becomes more flexible. The heel may throb at the end of a day as well.

When there is no resolution of acute plantar fasciitis pain, chronic plantar fasciitis or fasciosis may develop. In response to the long term presence of an inflammatory process, the plantar fascia may become thickened and develop fragmentation and degeneration at its heel attachment. Plantar fasciosis may develop as early as 6-10 months after the initial plantar fasciitis presentation. We used ultrasonography to quantify the size of the plantar fascia. A thickness of less than 0.4 cm is considered a normal plantar fascia measurement. The thickness of greater than 0.4 cm is considered pathologic and confirms the presence of plantar fasciosis/chronic plantar fasciitis. Plantar fasciitis is the most common cause of heel pain and accounts for 116%-15% of all foot problems requiring medical attention. Most cases of acute plantar fasciitis (90%) can be managed conservatively with stretches, ice, anti-inflammatory medications, and night splints, amongst other therapies. However, for 10% of the population with plantar fasciitis, it can become recurrent and traditional therapy options fail to help the heel pain. Chronic plantar fasciitis is also called plantar fasciosis. Current treatments for chronic plantar fasciitis include extra corporeal shock wave therapy (ultrasound), platelet rich plasma injections, open plantar fasciotomy, endoscopic plantar fasciotomy, and other invasive procedures. Satisfaction with these techniques range from 50-95%, but complications from surgical release of the plantar fascia can include a long recovery, nerve damage and numbness, wound infection, deep vein thrombosis from immobilization, calcaneal cuboid syndrome (lateral foot pain), metatarsal stress fractures, scar formation, and recurrent plantar fasciitis.

Fat grafting is a developing technology finding utility in filling of soft tissues, with over 70,000 such procedures in 2015. Fat grafting specialties include: plastic surgery; ear, nose, throat (ENT) and facial plastic surgery; ophthalmology or oculoplastic surgery; dermatology and cosmetic dermatology; oral and maxillofacial surgery; and aesthetic medicine. In fat grafting, autologous fat is obtained, for example, by liposuction techniques. The fat, obtained by liposuction or otherwise, is then separated into oil, fat, and aqueous fractions, with the fat fraction being used for therapeutic purposes. In one example, strainers are used to separate the fat fractions. In another, the fat is rolled in gauze, e.g., TELFA®. In further examples, the fat is fractionated by centrifugation. These current fractionation processes are costly, labor-intensive, and/or expose the fat to the environment, thereby increasing the risk of infection. LIP-IVAGE® is a vacuum filtration unit that is an improvement on the open-air systems, but requires a vacuum system and subsequent transfer to a delivery system. There is a need for rapid, easy-to-use, and inexpensive devices and techniques for harvesting and that minimize environmental exposure and exposure to multiple devices where each step adds expense, labor costs, and risk of contamination.

SUMMARY

According to one aspect of the invention, a fat grafting device is provided. The device comprises:
  a rotatable internal body having a lumen, an axis of rotation, a first end comprising a central outlet from the lumen, a porous wall configured to retain fat tissue or cells within the lumen and pass liquids through the wall, and a second end opposite the first end, having an opening;
  an external body surrounding and rotatably retaining the internal body, the external body having a first end comprising a cannula adaptor, such as a Luer adaptor, aligned with and optionally surrounding at least a portion of the central outlet of the internal body, and a second end opposite the first end, having an opening;
  a piston slidably disposed within the internal body and having a peripheral seal engaging an inner surface of the porous wall of the internal body;
  an internal plunger body attached to the piston and defining a central cavity;
  an external plunger body rotatably retaining the internal plunger body and disposed at the second end of the external body; and
  a drive assembly attached to the internal plunger body and comprising within the internal plunger body, either:
    a cylindrical plunger having spiral threads, a ratchet configured to engage the spiral threads of the plunger, and a retainer attached to the internal plunger body configured to engage the ratchet, or
    spiral threads on an inside surface of the internal plunger body, a plunger, and a ratchet affixed to the plunger so as to rotate in only one direction, the ratchet engaging the spiral threads on the inside surface of the internal plunger body,
  wherein the piston engages the internal body, so that when the internal plunger body and piston is rotated, the internal body rotates.

According to another aspect of the invention, a guide device adapted to a human foot, for use in identifying one or more plantar fascia landmarks is provided, comprising:
  a support member, comprising,
    a curved first portion adapted to or configured to receive a posterior surface of a heel, for example with a major surface on the inside of the curve, and having a lateral and a medial end;
    a second portion connected to and extending in an anterior direction from the medial end of the first portion, optionally having a major surface facing laterally or adapted to or configured to a medial side of a foot extending from the heel to the arch of the foot;
    a third portion connected to and extending from an anterior end of the second portion, adapted to or configured to the arch of a foot, e.g. comprising a twist in which the major surface of the support member rotates from facing in a lateral direction towards a side of the foot to facing in a superior direction towards the plantar surface of the foot; and a fourth portion connected to an end of the third portion opposite the second portion and extending towards toes of a foot, in an anterior direction from the third portion and optionally having a first major surface adapted to or configured to face a plantar surface of a foot, e.g. facing in a superior;

a heel guide adapted to or configured to cross a plantar surface of a heel, e.g., extending laterally from an inferior side of the first or second portion of the support member, and optionally wherein the heel guide is arcuate with an anterior concave side;

a guide member strip having a first end attached to the heel guide and a second end fastened to the fourth portion of the support member and defining a guide opening adapted to or configured to center over a landmark of the plantar fascia when the guide member is aligned over the planter fascia, optionally, with the guide member strip passing over the distal metatarsal head and calcaneus bone, wherein the landmark is an injection site on the plantar fascia, for example, an injection site for a corticosteroid, PRP (platelet-rich plasma), SVF (stromal vascular fraction), or fat cells or tissue.

In yet another aspect of the invention, a method of separating live fat cells and tissue from liquids is provided, comprising:

drawing live fat cells or fat tissue into the internal body of the device described above, or a syringe device according to any aspect described herein, by moving the piston axially away from the first end of the external body;

rotating the internal body of the device by moving the cylindrical plunger in an axial direction relative to the ratchet, thereby rotating the ratchet; and ejecting the fat cells or tissue from the internal body by moving the piston axially toward the first end of the external body.

According to a further aspect of the invention, a method of grafting live fat cells and tissue in a patient is provided, comprising:

drawing live fat cells or fat tissue through a cannula and into the internal body of the device described above, or a syringe device according to any aspect described herein, by moving the piston axially away from the first end of the external body;

rotating the internal body of the device by moving the cylindrical plunger in an axial direction relative to the ratchet, thereby rotating the ratchet; and injecting the fat cells or tissue from the internal body by moving the piston axially toward the first end of the external body.

According to another aspect of the invention, a method of treating plantar fasciitis in a patient, comprising injecting fat cells into the plantar fascia of the patient in an amount effective to treat plantar fasciitis in a patient. The method optionally utilized the device described above, or a syringe device according to any aspect described herein, and/or the guide device adapted to a human foot, for use in identifying one or more plantar fascia landmarks, according to any aspect described herein.

BRIEF DESCRIPTION OF THE DRAWINGS

The drawings provide depictions of various aspects of the devices and/or methods described herein and are intended only to be illustrative and non-limiting.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "comprising," "comprise" or "comprised," and variations thereof, are meant to be open ended. The terms "a" and "an" are intended to refer to one or more.

As used herein, the "treatment" or "treating" of a condition, wound, or defect means administration to a patient by any suitable dosage regimen, procedure and/or administration route of a composition, device or structure with the object of achieving a desirable clinical/medical end-point.

As used herein, the term "patient" or "subject" refers to members of the animal kingdom including but not limited to human beings and "mammal" refers to all mammals, including, but not limited to human beings.

As used herein, with respect to a stated location or landmark being "over" or "under" a specified anatomical structure, those terms do not refer to any fixed, specific directionality, other than referring to a position on an opposite side of the patient's skin to the stated anatomical structure, such as a bone, ligament, tendon, or plantar fascia). Likewise, reference to anatomical directions, such as anterior, posterior, axial, or medial, and reference to position relative to a user of the product, such as distal and proximal, are merely used to describe the relative orientation, configuration, adaptation, and arrangement of elements of a device or apparatus, and are not intended to be otherwise limiting, e.g., as requiring a fixed, spatial orientation of the device, such as relative to a specific patient or end user of the device.

Figure 1:
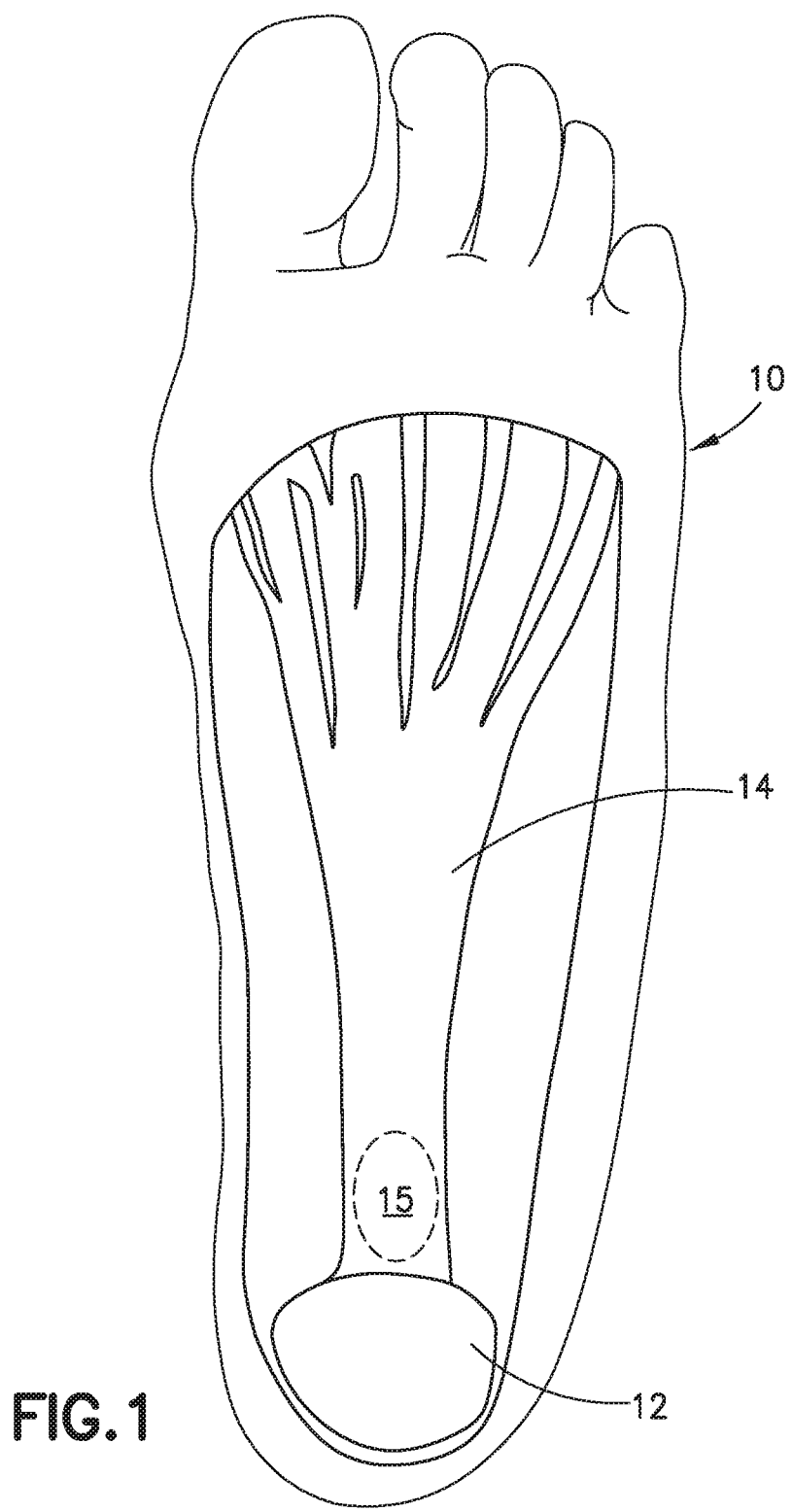
FIG. 1 is a cutaway view of a plantar side of a left foot showing the plantar fascia.

FIG. 1 is a cutaway view of the plantar sided of a human left foot 10, showing the (heel) calcaneus bone 12, plantar fascia 14 (also referred to as plantar aponeurosis), and the typical site of inflammation in plantar fasciitis 15. Provided herein is a device to facilitate treatment of plantar fasciitis by providing a simple external device for identifying location for corticosteroid injection as well as for the anti-fibrotic fat grafting method described herein.

The plantar fascia protractor is a device that is used to determine the location of the plantar fascia in the foot. It will allow for accurate determination of the location for injections of therapeutic compositions, such as steroids, PRP (platelet-rich plasma), SVF (stromal vascular fraction), or fat cells or tissue into the plantar fascia, for example, to treat acute or chronic plantar fasciitis.

Current determination of the location of the plantar fascia depends on either physical exam or use of ultrasound to identify its precise location. Injection of steroid into the wrong location in the heel can lead to fat pad atrophy, a devastating condition that creates chronic heel pain and inability to ambulate.

Chronic plantar fasciitis interventions currently involve more invasive surgical procedures. This device can be used as a surgical guide for less invasive percutaneous perforations with fat injections as described herein.

As described further in reference to FIGS. 2A-4, the device is first placed along the heel where there is a bend in the device and then the superior portion is placed along the first metatarsal bone. There is a twist in the device to alter the orientation along the medial side of the foot. The moveable protractor/compass arm is then able to be moved to follow the plantar fascia in the foot, thereby providing an accurate marker for various treatment options of the plantar fascia. It can be adjustable for different sized feet.

This cheap, reusable plastic or metal device can be used in the training of foot and ankle surgeons, podiatrists, as well as plastic surgeons, and even internal medicine doctors desiring to safely treat acute plantar fasciitis with steroids in their practice. While some podiatrists or foot and ankle surgeons may be comfortable with the foot anatomy, steroid injections are often misplaced leading to devastating fat pad loss. In addition, plastic surgeons or any surgeon attempting our novel technique of plantar fascia perforating fat injections can be aided in the exact location despite precise knowledge of foot anatomy.

Other plantar fascia marking devices are primarily used for determining the endoscopic approach to plantar fascia release. This is done with a lateral approach. Our design is different in that we focus on a plantar approach for identifying the location of the plantar fascia for various minimally invasive procedures. This device obviates the need for ultrasound devices and helps the physician to verify injection location for steroid, thereby avoiding inadvertent injection into the fat pad.

Figure 2A:
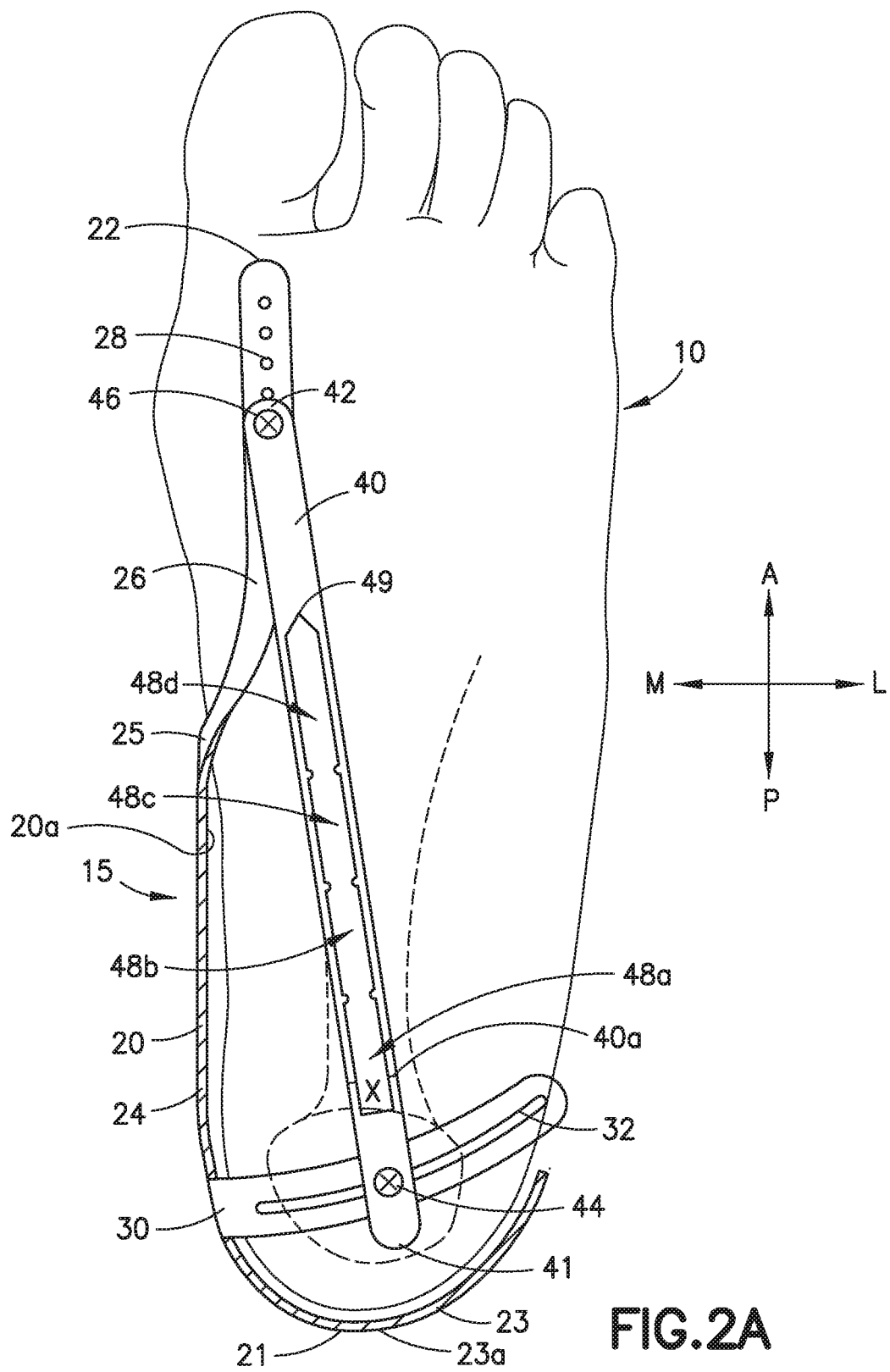
FIGS. 2A and 2B depict one aspect or embodiment of a guide device as described herein, with FIG. 2A providing a plantar view of the device, and FIG. 2B providing an elevation view of the device placed on a human foot.
Figure 2B:
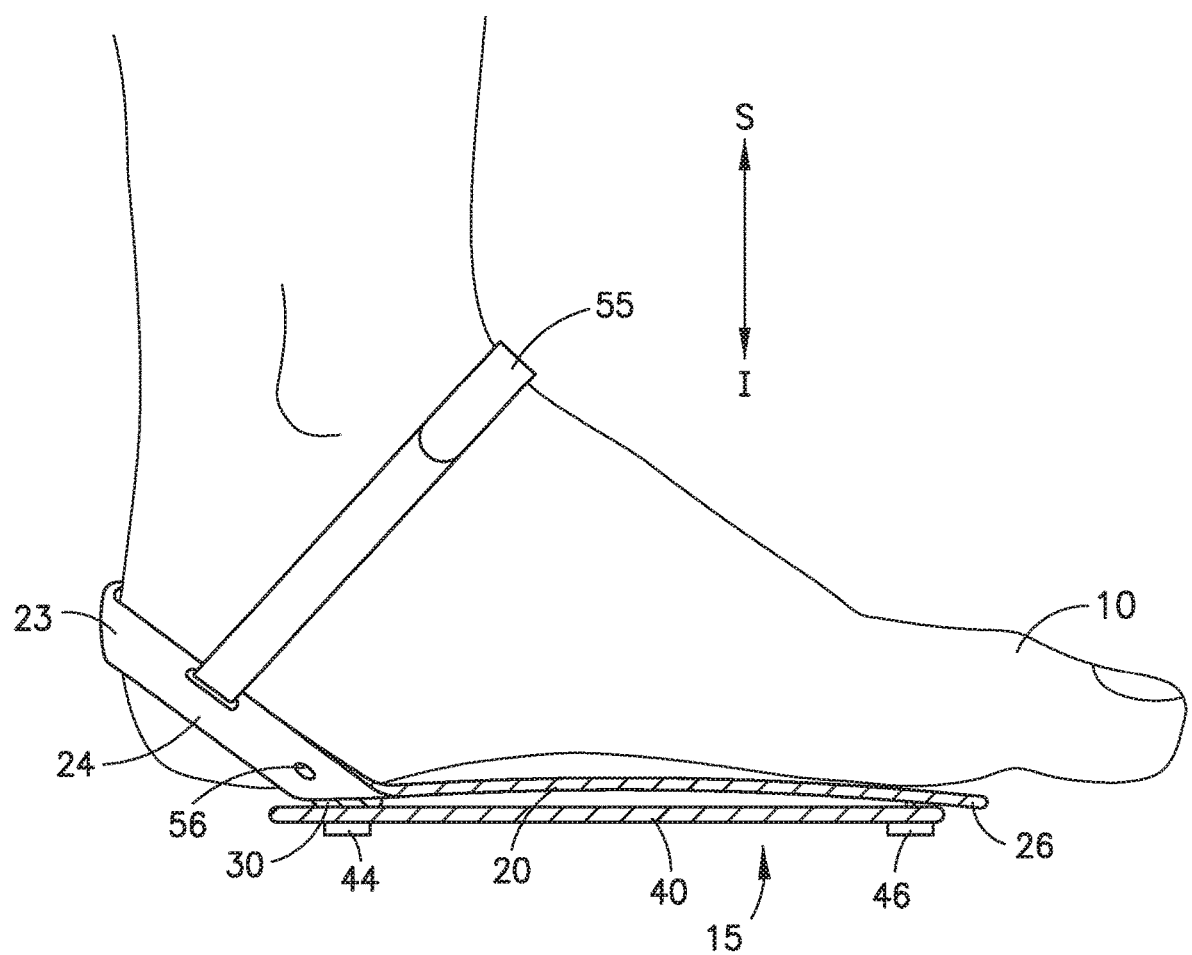

In one aspect, a device is provided for locating internal landmarks for treatment of plantar fasciitis. For ease of reference, directionality of the device as depicted in FIGS. 2A-4 is in reference to standard anatomical directions when the device is placed on a human body, namely: anterior (A, towards the front), posterior (P, towards the back), medial (M, towards the midline of the body), and lateral (L, away from the midline of the body), as shown in FIGS. 2A and 4, superior (S, towards the head), and inferior (I, towards the bottom of the feet), as shown in FIG. 2B, and any recitation of direction herein, unless otherwise indicated, does not refer to a direction relative to the center of the earth or any object external to the device. Further, when an element, portion, or component is said to extend in a specific direction, it does not exclude that the element, portion or component may not be linear or also extends in part in another direction. For example, a portion that extends in an anterior direction may also partly extend in a medial or lateral and/or in a superior or inferior direction.

In one aspect, depicted in FIG. 2A, a device 15 is depicted on a plantar side of a left foot 10. The device 15 comprises a support member 20 having a first end 21, a second end 22, first portion 23, a second portion 24, a third portion 25, and a fourth portion 26.

Referring to FIG. 2A, the first portion 23 is arcuate and is adapted to, or configured to, fit around and against a heel of a foot, extending from a lateral side to a medial side of the heel. The second portion 24 is connected to the anterior, medial end of the first portion 23 and is configured to extend along the side of the foot in an anterior direction towards the second end 22 of the support member 20. The third portion 25 is connected to an anterior end of the second portion 24 opposite the first portion 23, and is configured to extend from the medial side, and along a surface of the arch of the left foot 10 to a plantar surface of the left foot 10. The fourth portion 26 of the support member 20 is connected to the anterior end of the third portion 25, and extends in an anterior direction to the second end 22, and over the distal first metatarsal head at the joint of the first metatarsal and phalanges bone on the plantar surface of the left foot 10.

The fourth portion 26 is a strip having a major surface configured to contact and/or be in a plane substantially parallel to plantar surface of the left foot 10. In the context of a strip of metal or other material, the strip has two major surfaces and two edges, where the width of the major surfaces, are substantially, e.g., at least 5-fold, greater than the thickness of the strip. For illustration, a major surface 20a of support member 20 is shown. The support member 20 is twisted at the third portion 25 so that the first major surface of the fourth portion 26 is on a plane transverse to a plane of a major surface of the second portion 24. In practice, the support member 20 may be twisted at the third portion 25 so that the first major surface of the fourth portion 26 is on a plane at an angle to, e.g., at an angle ranging from 75° to 90°, with respect to a plane of a major surface of the second portion 24. The fourth portion 26 comprises guide holes 28, e.g., threaded holes adapted to receive a fastener.

An arcuate heel guide 30 is shown in FIG. 2A connected to the support member 20. The heel guide 30 is a metal strip having a major surface configured to cross the heel of the left foot 10, and, as shown contacting or parallel to a plantar surface of the heel of the left foot 10, and as shown, passing over the calcaneus bone (in phantom) of the left foot 10. The major surface of the heel guide 30 is substantially parallel to a major surface of the fourth portion 26. A curved slot 32 is defined by the heel guide 30.

Guide member 40 having a proximal end 41 and a distal end 42, is affixed to heel guide 30 at its proximal end 41 by a first releasable fastener 44 and is affixed to the fourth portion 26 of the support member 20 at distal end 42 by second releasable fastener 46. The first and second releasable fasteners 44, 46 can be any fastener that can be transitioned from an engaged position and a non-engaged position, such as a nut and bolt, a nut and a retained bolt, a spring-loaded pin, a screw, a friction fitting, or a clip. Suitable fasteners or retainers are broadly-known in the mechanical arts. First releasable fastener 44 can either be in an engaged position, where it retains the position of the guide member 40 relative to the heel guide 30, and a non-engaged position, where the guide member 40 can be moved relative to the heel guide 30. Likewise, second releasable fastener 46 can either be in an engaged position, where it retains the position of the guide member 40 relative to the support member 20, and a non-engaged position, where the guide member 40 can be moved relative to the support member 20. As shown, the fastener 44 used to connect the guide member 40 to the heel guide 30 is a friction fitting retained by the guide member 40 and passing through the curved slot 32, and terminating with a friction fitting that engages the heel guide 30 when turned in one direction and disengages the heel guide 30 when turned in a different direction. Fastener 46 is a retained screw that engages guide holes 28 when screwed in, and disengages when unscrewed. Guide member 40 also defines injection guide openings 48a, 48b, 48c, and 48d, passing through the guide member. Injection guide opening 48d is shown as having a centering guide 49. Corticosteroid injection site, located approximately three finger widths, e.g., 2", from the posterior end 23a of the device 15, is marked with an X on the plantar surface of the foot 10, and also is denoted by a marking 48a on the guide member 40. Once the foot 10 is marked with an X or equivalent marking, the device 15 can be removed from the foot 10 prior to injection.

In use, device 15 is placed on the left foot of a patient, with the first portion 23 of the support member placed on the heel of the patient, and the fourth portion 26 passing over the distal head of first metatarsal bone. The distal end 42 of the guide member 40 is fastened and retained in position at the distal head of first metatarsal bone, and the proximal end 41 of the guide member 40 is fastened and retained in position over the calcaneus bone of the patient, so that the injection guide openings pass over the plantar fascia. Positioning of the guide member 40 may be facilitated by flexion of the big toe of the left foot 10 to expose the position of the medial component of the plantar fascia. Prior to placement of the device 15 on the foot 10, a line or other mark can be drawn on the patient's foot identifying the location of the medial component of the plantar fascia, and then the device can be placed on the patient's foot and the guide member is aligned over the mark. In use, for example, for corticosteroid, PRP, SVF, or fat cells or tissue injection, e.g., as described herein, the device can be retained in place, for example, by holding the device in place, or by taping the support member 20 to the patient's foot, and injections can be guided by the injection guide openings 48a, 48b, 48c, and 48d. Injection guide opening 48a falls over the posterior portion of the plantar fascia adjacent to the attachment of the plantar fascia to the calcaneus tuberosity, for example and without limitation, within 1.75 to 2.25 inches, e.g., within two inches from the posterior end of the device, for example, extending from 0.5 to 2 inches from the attachment of the plantar fascia to the calcaneus tuberosity and/or the fastener 44. Injection guide openings 48a, 48b, 48c, and 48d can be used to locate sites for injection of corticosteroid, PRP, SVF, or fat cells or tissue, e.g., as described below, in treatment of plantar fasciitis. Alternatively, the device 15 can be placed in position, the guide member 40 adjusted as indicated above, and one or more of injection guide openings 48a, 48b, 48c, and 48d can be used as stencils, such that a practitioner can trace the outlines of one or more of injection guide openings 48a, 48b, 48c, and 48d on the foot of a patient, and the device is removed prior to injection.

FIG. 2B provides an elevation view of the device 15 of FIG. 2A, with like reference numbers representing the same structure. Although not shown for clarity in FIG. 2A, hook and loop fastener 55 (e.g., a VELCRO® fastener) is shown in FIG. 2B, which is used to hold the device in place on the foot 10. The elevation view of the device 15 of FIG. 2B also depicts a medial guide hole 56 or injection guide for medial injection of corticosteroids. Additional straps, hook and loop fasteners, strings, belts, or equivalent structures of any composition or structure may be integrated into the device 15 and used to further secure the device in place. FIG. 2B illustrates the bending of the support member 20 at the third position 25' with the first portion 23' being superior to the third and fourth positions 25' and 26'. In one aspect, the medial guide member 56 and first injection guide opening 48a are located at three finger widths, or 1.5" to 2.5", e.g., 2" from the posterior end of the device 15.

Figure 3:
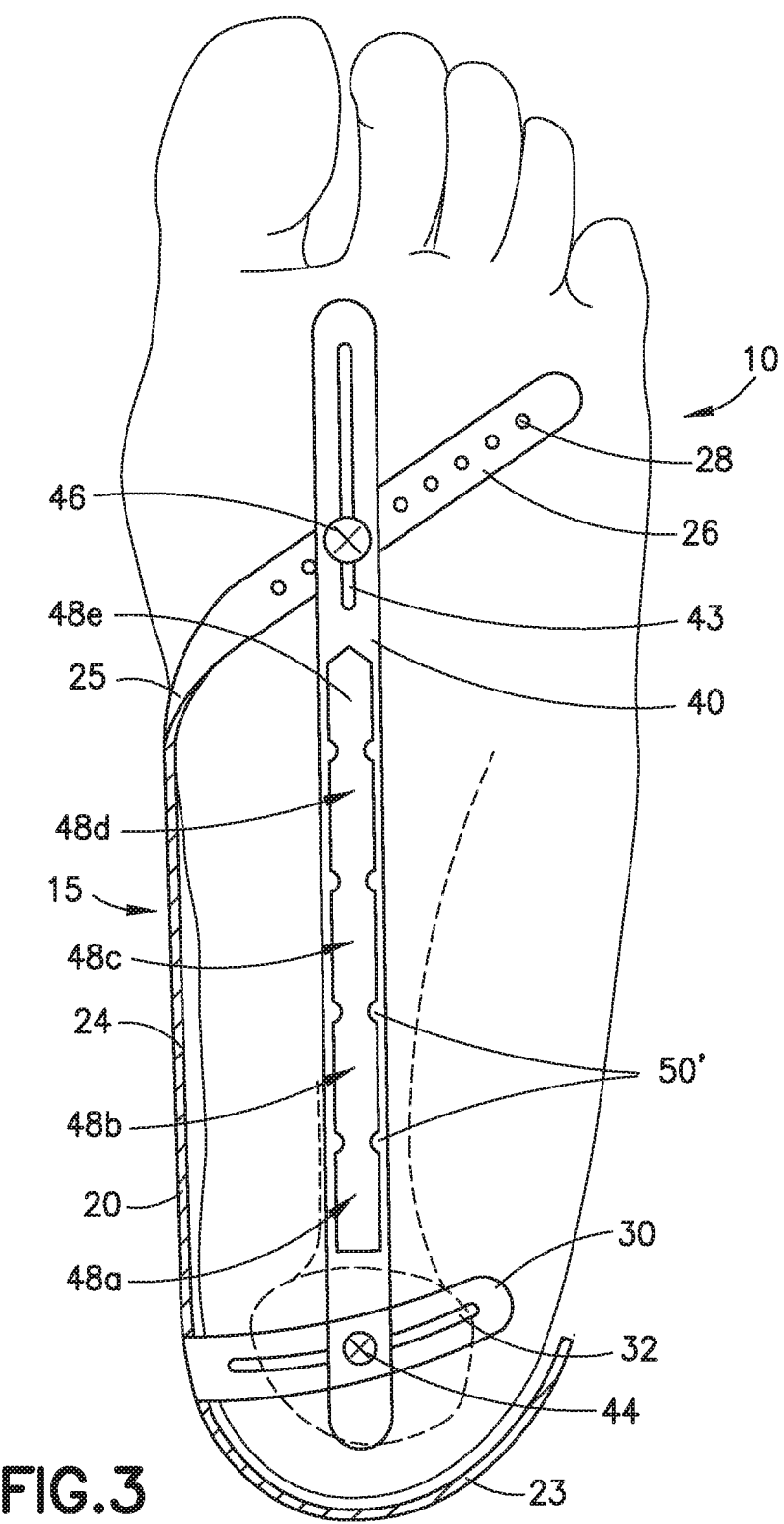
FIG. 3 depicts a second aspect or embodiment of a guide device as described herein.
Figure 4:
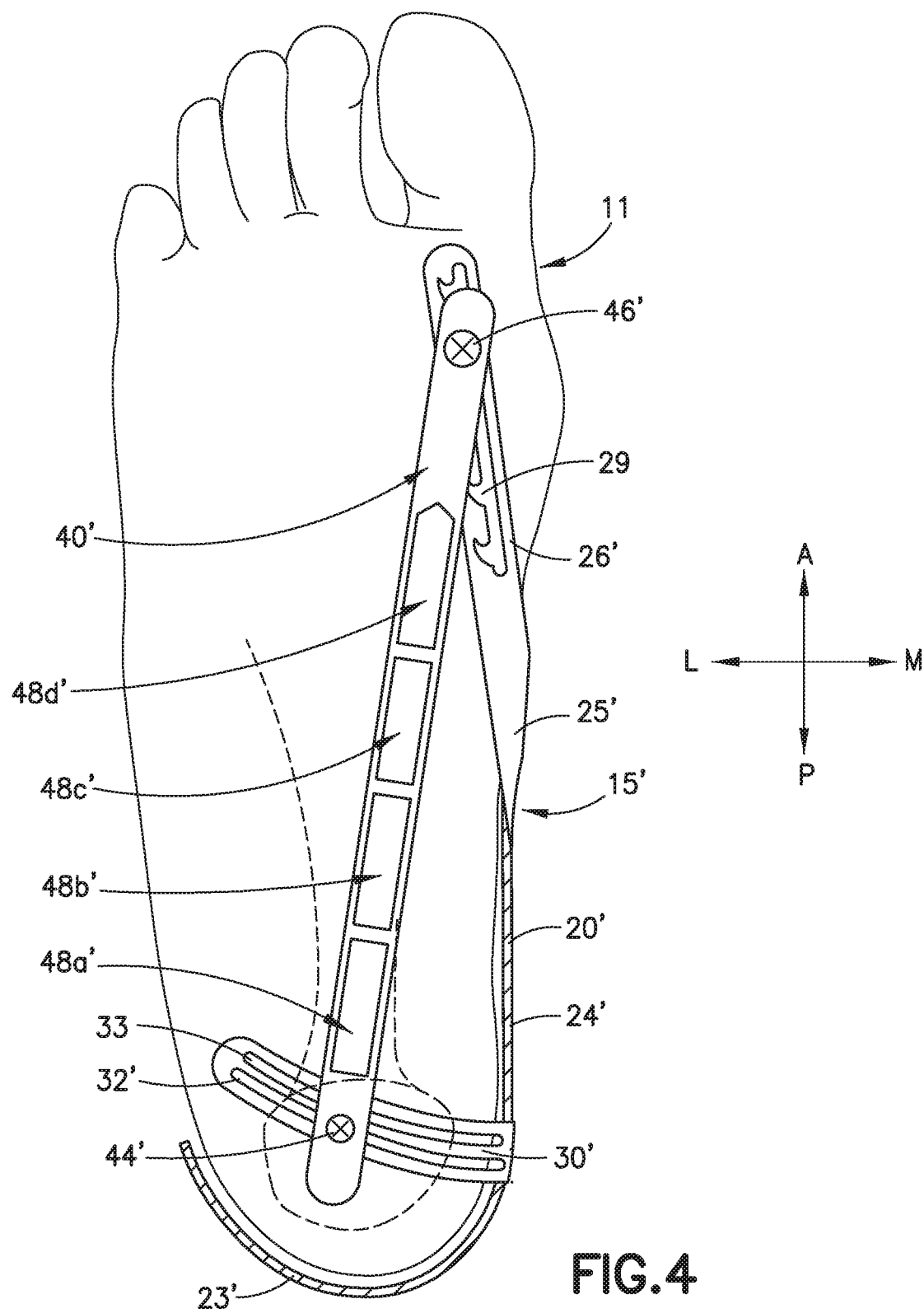
FIG. 4 depicts a further aspect or embodiment of a guide device as described herein.

FIG. 3 depicts an alternative version of the device depicted in FIG. 2, with like numbers referencing like elements. In the device of FIG. 3, the fourth portion 26 of the support member extends diagonally in a lateral and medial direction. In contrast to the device depicted in FIG. 2, the guide member 40 defines a slot in which fastener 46 slides when not engaged. Guide member 40 also defines an additional injection guide opening 48e, and injection guide openings 48a, 48b, 48c, 48d, and 48e are not fully separated, but are part of a contiguous opening injection in which injection guide openings 48a, 48b, 48c, 48d, and 48e distinguished by notches 50 in the guide member 40.

FIG. 4 depicts an alternative version of the device depicted in FIGS. 2A and 2B, but adapted to a patient's right foot 11, with reference numbers for like elements depicted in FIG. 2A being identified by an apostrophe. Thus the device 15' includes: a support member 20' having a first, second, third and fourth portion, 23', 24', 25', and 26', respectively, a heel guide 30', comprising a slot 32', but also comprising a second slot 33, for increased flexibility in fitting to a patient's foot, a guide member 40' defining injection guide openings 48a', 48b', 48c', and 48d', fasteners 44' and 46'. Fastener 44' is shown fitted within slot 32', but can be released and removed from slot 32', and inserted through second slot 33, to extend the guide member 40' in an anterior direction. As opposed to the holes 28 of the device of FIG. 2A, a notched slot 29 is provided in the device of FIG. 4, and in use, when the device 15' is fitted to a patient's foot, the fastener 44' is moved along and between slots 32' and 33, and within notched slot 29 until the guide member 40' is appropriately positioned over the patient's plantar fascia.

Referring to FIGS. 2A-4, the support member 20, 20', the heel guide 30, 30' and the guide member 40, 40' are rigid or substantially rigid metal strips that are of sufficient thickness to prevent substantial deformation during use and storage. The support member 20, 20', the heel guide 30, 30', and the guide member 40 40' may be manufactured independently from the same or different material. In one aspect, the support member 20, 20', the heel guide 30, 30', and the guide member 40 40' are metallic, for example, are manufactured from a stainless steel, though in practice, the support member 20, 20', the heel guide 30, 30', and the guide member 40 40' may be of any suitable material, such as, without limitation, a metal, a metal alloy, a ceramic, a polymer or plastic, carbon fiber, or compositions or composites thereof. Practically, because the device is used in a patient setting, it should be constructed of a material that is amenable to sterilization either by heat, chemical, or by any other acceptable means.

As would be recognized by one of ordinary skill, devices depicted in FIGS. 2A-4 function in essentially the same manner, and components or elements thereof interact in essentially the same manner, and the device and elements thereof may be manufactured from any material as indicated for any aspect of the device of FIGS. 2A-4. Likewise, different elements, shapes, and structures depicted in FIGS. 2A-4 may be interchanged.

The devices depicted in FIGS. 2A-4 are for illustration, and may be manufactured in any suitable size, with the location, size, and number of holes, slots, or fasteners, or the overall geometry of the device being variable and optimizable.

In another aspect, a "push to spin" syringe is provided that will allow aspiration of fat, centrifugation, and injection back into a patient in a single device without contamination. Current methods of fat harvest from liposuction involves transferring fat from syringes to other devices for processing prior to injection back into the patient for autologous fat grafting. Most current systems are extremely expensive, time consuming, or cumbersome. The device allows for adequate negative pressure to evacuate the fat, has a lock that enables a push top to spin the micro-porous inner chamber, which allows fluid removal from the lipoaspirate to help purify the fat. The fat can then be injected directly back into the patient from the same device. This device is ideal for office procedures of fat grafting including facial aesthetics and general reconstruction, including breast cancer reconstruction. End users include plastic surgeons, ENT, oral maxillofacial, dermatologists, oculoplastic surgeons, and aesthetic medicine specialists.

With a single device, the fat is aspirated and then can be reinjected into the patient without exposure of the fat. Current methods require TELFA® rolling the fat open to air, centrifuging open to air and wicking with gauze, using strainers, requiring a vacuum, or complicated tubed systems to purify the fat. This device can be manufactured inexpensively from typical plastics and other materials, such as polymers, silicones, ceramics, metals, etc., commonly used for production of medical syringes and medical devices in general, and as such, in one aspect, is intended to be disposable after a single use, or multiple uses in a patient. This device optionally is reusable, either with the same patient, or if constructed of suitable materials able to withstand sterilization, between patients, which will save practices money, does not require transfer to another syringe for injection, and will allow for easy use in the office for small volume fat grafting procedures such as facial augmentation, fat grafting to the foot or hand, breast, or other cosmetic or reconstructive indications.

Figure 5:
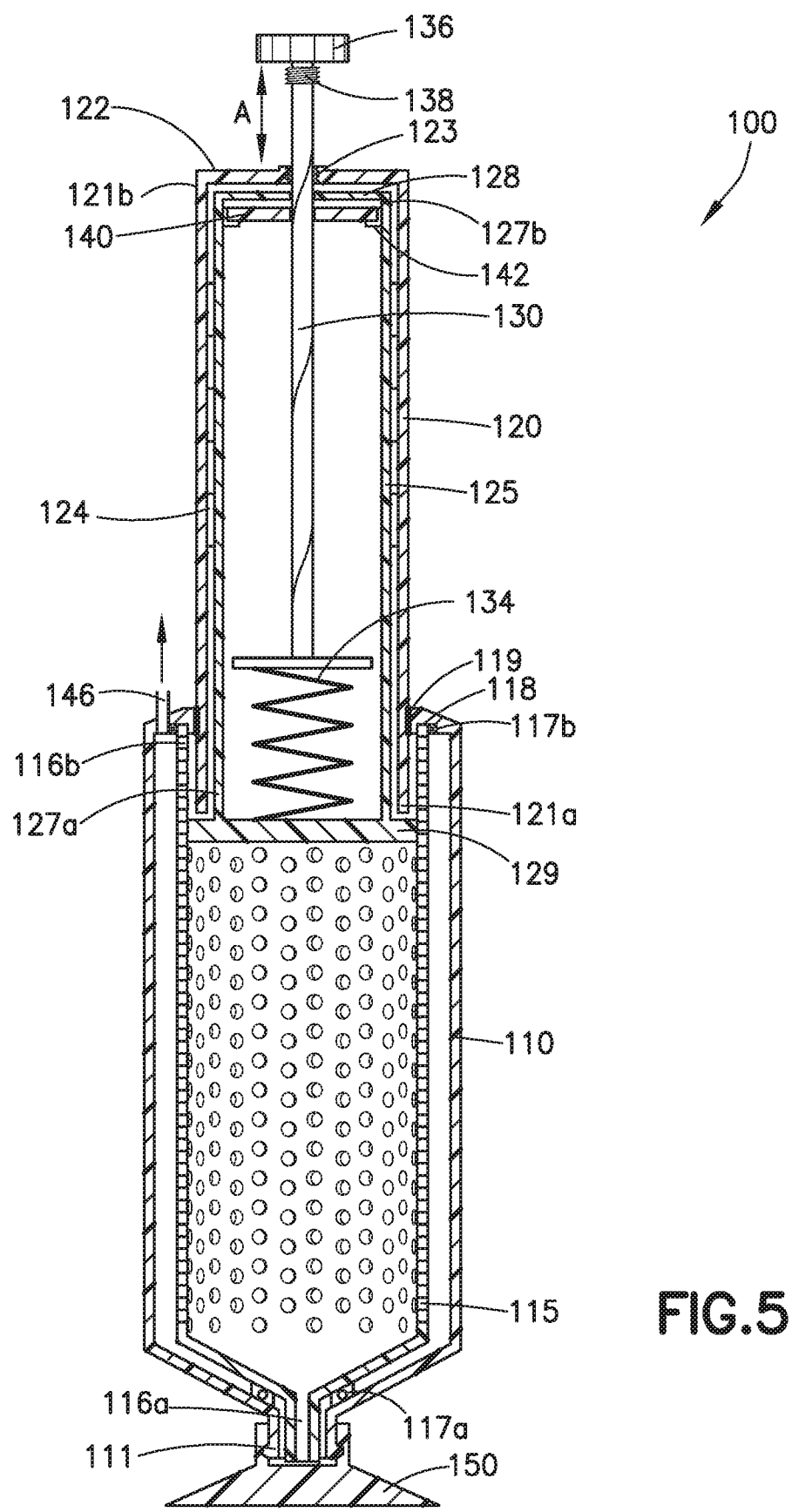
FIG. 5 is a cross-sectional view of one aspect or embodiment of a fat processing device as described herein.

FIG. 5 depicts a "push-to-spin" syringe 100, for obtaining, processing, and delivering live fat (adipose) tissue for transplant purposes. The syringe 100 comprises an external body 110, having a Luer adaptor 111, such as a slip or locking adaptor, and a cylindrical, porous internal body 115 having a first opening 116a that protrudes at least partially into the Luer adapter 111, and a second opening 116b of essentially the same diameter as the internal body 115. As would be recognized to one of ordinary skill, a Luer adaptor is merely exemplary, and any suitable locking or non-locking adaptor may be configured into the device. Bearings 117a and 117b support the internal body 115, allowing the internal body 115 to spin freely within the external body 110. The external body 110 has a second opening 118 at an end opposite the Luer adaptor 111, comprising seals 119, such as ridged silicone seals.

A cylindrical external plunger body 120 is shown in FIG. 5, having an outside diameter smaller than an inside diameter of the internal body 115 and which passes through the second opening 118 of the external body 110. The external plunger body 120 has a first end 121a that extends into the internal body 115 and is slidably engaged by the seal 119, and can be otherwise retained within the second opening 118. The external plunger body 120 also has a second end 121b with a cap portion 122 defining a threaded opening 123. Needle bearings 124 are shown affixed to an internal wall of the external plunger body.

The internal body 115 and internal plunger body 125 are rotatably retained within the external body 110 and the external plunger body 120, respectively. By "rotatably retained" it is meant retaining the internal body in a manner that permits rotation of the internal body about a central axis within the external body, e.g., with one or more bearings. As used herein, a "bearing" can be either a mechanical assembly of rolling objects, such as spheres or cylinders and a retainer for the rolling objects, or any other structure that permits free movement, e.g., rotation in the context of the device, of one mechanical part in relation to another, and includes other useful structures, such as abutting low friction surfaces.

In FIG. 5, the internal body 115 and internal plunger body 125 are retained by bearings, which are broadly-known in the mechanical arts, and suitable bearings, with suitable physical tolerances, can be utilized in the device 110. For example, needle bearing 124 would be selected so as to have sufficient axial retention strength so as to withstand typical axial forces applied during use of the device. Different bearing types may be substituted, as there are a large variety of bearings and bearing types known to those of ordinary skill. Further, bearings may be omitted where appropriate, and in their place, low-friction surfaces may be employed, such as polytetrafluoroethylene (PTFE) or graphene surfaces, for example, at the first end 116a of the internal body 115 where it meets the external body 110, both abutting surfaces may comprise a layer of PTFE, graphene, or other low friction materials.

A cylindrical internal plunger body 125 is depicted, fitting at least in part within the external plunger body 120 and engaging the needle bearings 124, thereby spinning freely within the external plunger body. The needle bearings 124 further retain the internal plunger body 125 from moving axially within the external plunger body 120. The internal plunger body 125 has a first end 127a extending within the internal body beyond the first end 121a of the external plunger body, and a second end 127b adjacent to the second end 121b or the external plunger body 120. A piston 129 is connected to the first end 127a or the internal plunger body 125 and slidably engages the internal wall of the internal body 115 so that materials, such as fat cells or tissue, within the internal body can be forced through the first opening 116a by pushing the piston 129 towards the first opening. The piston 129 may be a standard medical syringe piston comprising ridged silicone or other polymeric material. FIG. 5 depicts the piston 129 in a first position at or near the second opening 116b of the internal body 115. Although the piston 129 engages the internal wall of the internal body 115 irrespective of its position within the internal body, when the piston 129 is in this first position, it should have sufficient friction or engagement with the internal wall of the internal body 115 so that spinning of the internal plunger body 125, and therefore the piston 129 results in spinning of the internal body 115. To this end, the diameter of a portion of the inner wall of the internal body may narrow at a point of engagement of the piston 129 in its first position, with the internal body 115, or notches, gears, protuberance(s), or any other suitable retaining member may be provided in the internal body, and a mating structure may be provided in the piston 129, to adequately engage such notches, gears, protuberance(s), or other structure of the internal body 115 to effectively engage the piston 129 so that spinning of the internal plunger body 120 results in spinning of the internal body 115.

As shown in FIG. 5, a plunger is used to spin the internal plunger body 125, and thereby spinning of the internal body 115. A suitable, simple mechanical system for use in spinning the internal body 115 is depicted in U.S. Pat. No. 7,111,546, relating to a salad spinner. A cylindrical plunger 130 having spiral threads depicted in FIG. 5, the plunger 130 is connected to a spacer 132 at one end and extends external to the external plunger body 120. The plunger 130 moves within threaded opening 123 as shown by arrows A in FIG. 5, toward and away from the piston 129, with a compression spring 134 biasing the plunger 130 away from the piston 129, and returning the plunger 130 to a first position away from the piston. The plunger 130 is connected to a knob 136 external to the external plunger body 120 and a threaded base 138 that engages the threaded opening 123 of the external plunger body 120 to lock the plunger 130 in place relative to the external plunger body 120. The external body 110, the external plunger body 120, and/or the knob 136 may be configured with suitable hand or finger grips or loops, or have modified surfaces, to facilitate gripping and use of the device.

A ratchet 140 is shown coaxial to the plunger 130, having a slot, threads, or other mechanism for engaging in a screw-type manner with the plunger 130, and spinning relative to the plunger 130 with axial motion of the plunger 130. In one non-limiting example, a "ratchet" is a mechanism that consists of a bar or wheel having inclined teeth into which a pawl drops so that motion can be imparted to the wheel or bar, governed, or prevented to allow effective motion in one direction only, or an equivalent structure permitting engagement in one direction of rotation and not in a second, opposite direction of rotation. In the context of the device described herein, a ratchet includes any mechanical or electromechanical structure that allows the ratchet, plunger, and internal plunger body combination to engage, and thereby spinning the ratchet in one direction and rotating the internal plunger body when the plunger is pressed, and the ratchet, plunger, and internal plunger body combination disengages when the plunger is pulled or otherwise biased in a direction opposite the body of the device, thereby allowing the plunger to be extended without stopping or reversing the rotation of the internal plunger body. It is noted that when a ratchet is used, the direction in which the ratchet can engage either when the plunger is pressed, or when the plunger is pulled, or biased away from the external body by, e.g., a compression spring. In one aspect, the ratchet engages, and causes rotation of the internal body when the plunger is biased away from the external body by, e.g., a compression spring, so as to control the speed of rotation of the inner body by virtue of the compression force of the spring and the angle or pitch of the spiral threads.

The internal plunger body 125 comprises a retainer 142 configured to retain the ratchet 140 in place within the internal plunger body 125, and to engage the ratchet 140 in a first spin direction and thus spin the internal plunger body, when the plunger 130 travels in a direction towards the piston 129, and to not engage the ratchet 140 in a second spin direction, allowing the ratchet 140 to spin freely within the retainer 142 without applying any substantial rotational force to the internal plunger body 125, such that pressing the plunger 130 towards the piston 129 spins the internal plunger body 125 and therefore the internal body 115, and the internal plunger body 125 and internal body 115 remain spinning as the plunger is biased towards the first position by the compression spring 134. It should be recognized by those of ordinary skill in the mechanical arts that use of a threaded base 138 of the knob 136 engaging the threaded opening 123, are only examples of the many possible alternative locking mechanisms for permitting movement of the piston 129 without spinning the internal body 115. Further, the threaded opening 123 and threaded base 138 are not entirely necessary for functioning of the device 110, but retention of the knob 136 close to the external plunger body 120, and preventing rotation of the internal body 115 may be desirable in use.

Outlet 146 is shown at a shoulder of the external body 110, though can be placed at any suitable position, and can be in the form of a tube extending within the external body 110. The outlet 146 is a draining port for draining or aspirating liquids or other material from the external body 110 during use. More than one outlets can be utilized to facilitate drainage. These outlets may have caps or locks to maintain negative pressure when aspirating fat.

Figure 6:
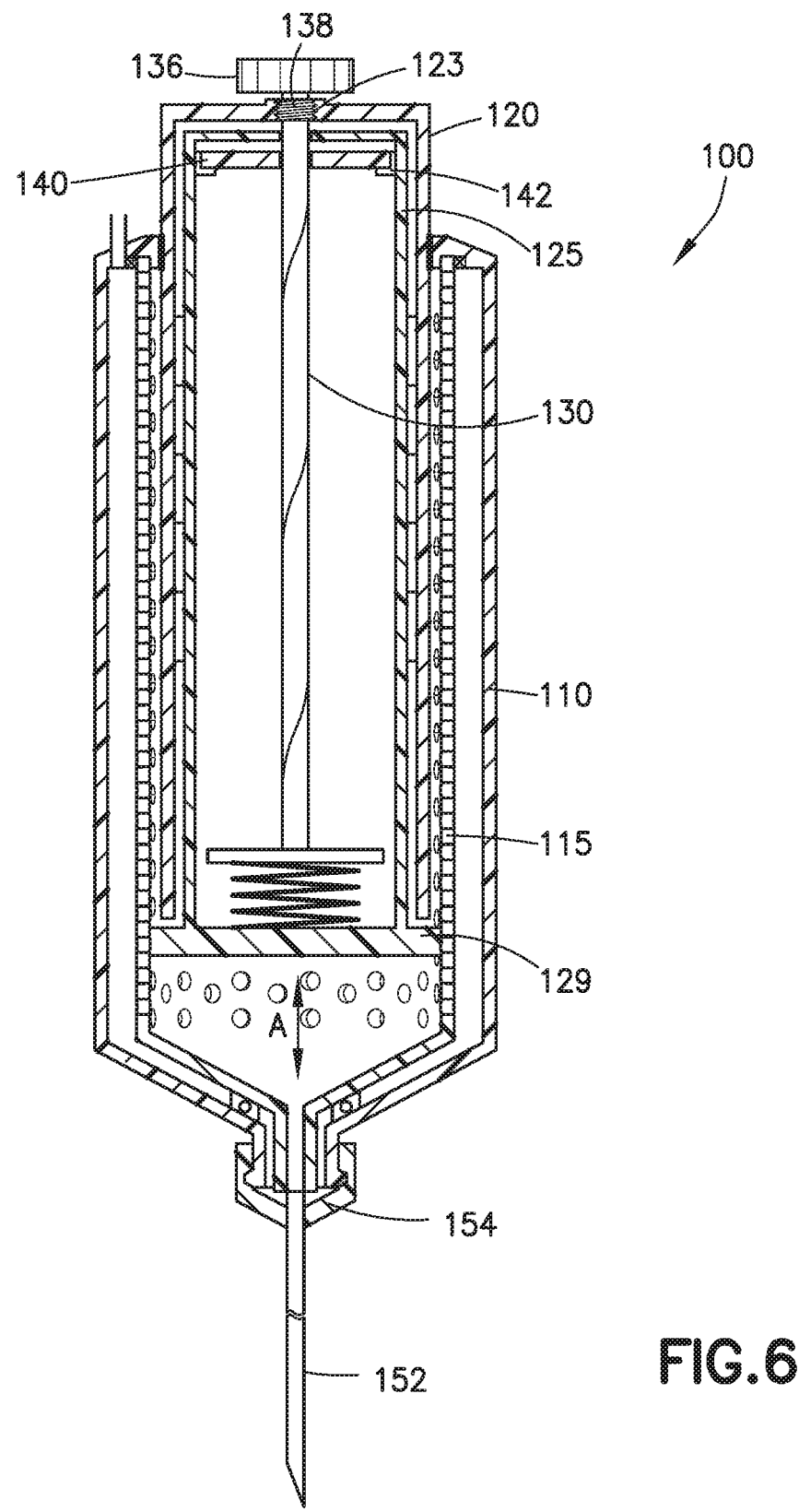
FIG. 6 is a cross-sectional view of one aspect or embodiment of a fat processing device essentially as described in reference to FIG. 5.

FIG. 6 depicts the device 100 of FIG. 5, with the external plunger body 120, the internal plunger body 125, the piston 129, and the plunger 130 in a second position for either aspirating fat tissue from a patient, or for delivering fat tissue to a patient. Like reference numbers in FIGS. 5 and 6 refer to like structures. In this position, the threaded base 138 of the knob 136 engages the threaded opening 123, so that the knob 136 and external plunger body 125 move together axially. In the configuration of FIG. 6, movement of the knob 136, or external plunger body 120 relative to the external body 110 will move the piston 129 in an axial direction either towards or away from the first opening 116*a* and the Luer adaptor 111. Also shown in FIG. 6 is a cannula (needle) 152, with a female Luer adaptor 154.

The exterior body 110 may be any suitable shape, though, typically it is cylindrical. The wall of the internal body 115 is porous, with pores, slots, or holes that are small enough to retain live adipose cells and tissue within the internal body while the internal body 115 is spinning, and permitting liquids to pass to the exterior of the internal body 115 without clogging. Suitable materials or structures for the walls of the internal body would be apparent to those of ordinary skill, and include, without limitation: slotted or perforated materials, meshes, porous polymers, or porous sintered metals, generally with openings generally less than 100 μM in width or diameter. Meshes may be supported by a porous framework of any suitable configuration in the wall of the internal body 115 external to the mesh.

The device 100 may be any useful size or volume. While the device 100 in aspects, is sized to facilitate easy handling with two hands, the volume of the device 100, e.g., the volume of the exterior body 110 or interior body may range from, for example and without limitation, 1 cc (cubic centimeters) to 100 cc, e.g., 1, 2, 5, 10, 15, 20, 25, 30, 35, 40, 45, 50, 55, 60, 65, 70, 75, or 100 cc.

In use, the device 100 is fitted with a cannula 152, the threaded base 138 of the knob 136 engages the threaded opening 123 so that the knob 136, the internal plunger body 125, and piston 129 are compact, and move together in an axial direction. This configuration is shown in FIG. 6. To draw fat tissue from a patient, the cannula 152 is inserted into a fat deposit in the patient and the fat tissue is drawn from the patient as in typical liposuction techniques, by axially drawing the knob 136 or external plunger body 120, and therefore the piston 129 away from the first opening 116*a*, producing negative pressure within the external body 110.

Once a sufficient amount of fat is drawn from the patient, the cannula 152 is removed from the patient and is removed from the device 100. The device 100 is placed into a stand 150, as shown in FIG. 5, the threaded base 138 of the knob 136 is unscrewed and released from the threaded opening 123 so that the knob 136 and plunger 130 move independently in an axial direction. Pumping of the knob 136, and therefore the plunger 130, causes the ratchet 140, and therefore the retainer 142, the internal plunger body 125, and the piston 129 to rotate in one direction. Due to engagement of the piston 129 with the inner body 115, the inner body 115 spins, with inertia forcing liquids through the openings in the wall of the inner body 115, and the inner body 115 retaining fat cells and tissue. Liquids are aspirated or otherwise drained or removed through opening 146 in the external body 110.

When sufficient fats and aqueous liquids are separated from the fat tissue, a fresh cannula 152 is attached to the device 100, the threaded base 138 of the knob 136 is screwed into the threaded opening 123 to restrict motion of the plunger 130, and the cannula is inserted at a site in a patient for delivery of the fat cells or tissue. The knob 136 is pressed axially towards the first opening 116a, thereby delivering the fat cells or tissue to the patient.

Also provided herein is a method of transplanting, e.g., autologous fat tissue, comprising: obtaining fat tissue or fat cells from a patient using a device 100 as described above, or an equivalent device, separating the fat tissue or cells from acellular liquids, such as lipids and aqueous liquids using that device, and injecting cells into a site of a patient using the device. The device is used as described above in the context of FIGS. 5 and 6.

Figure 7A:
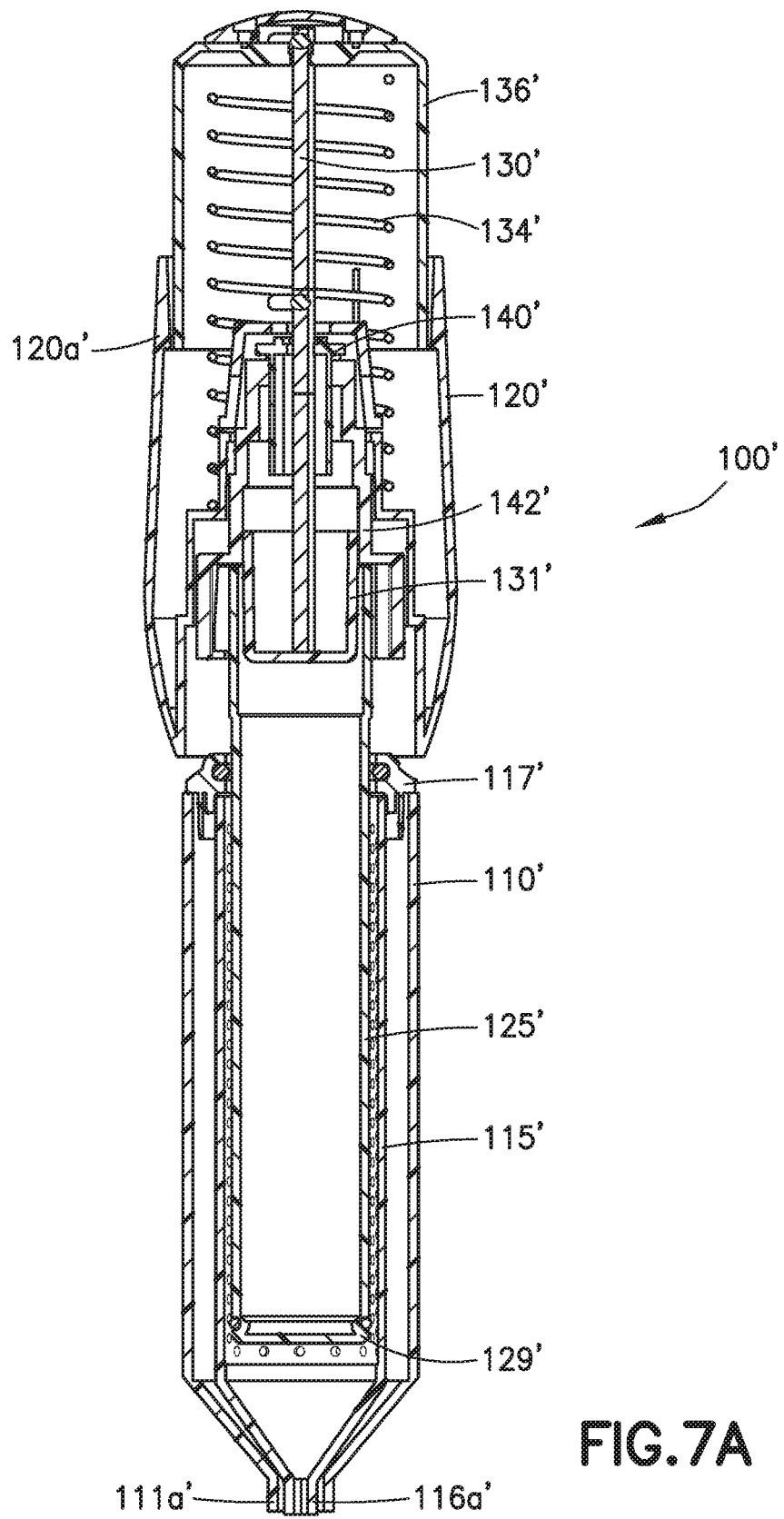
FIGS. 7A and 7B are a cross sectional and an exploded view, respectively, of one aspect of a fat processing device as described herein.
Figure 7B:
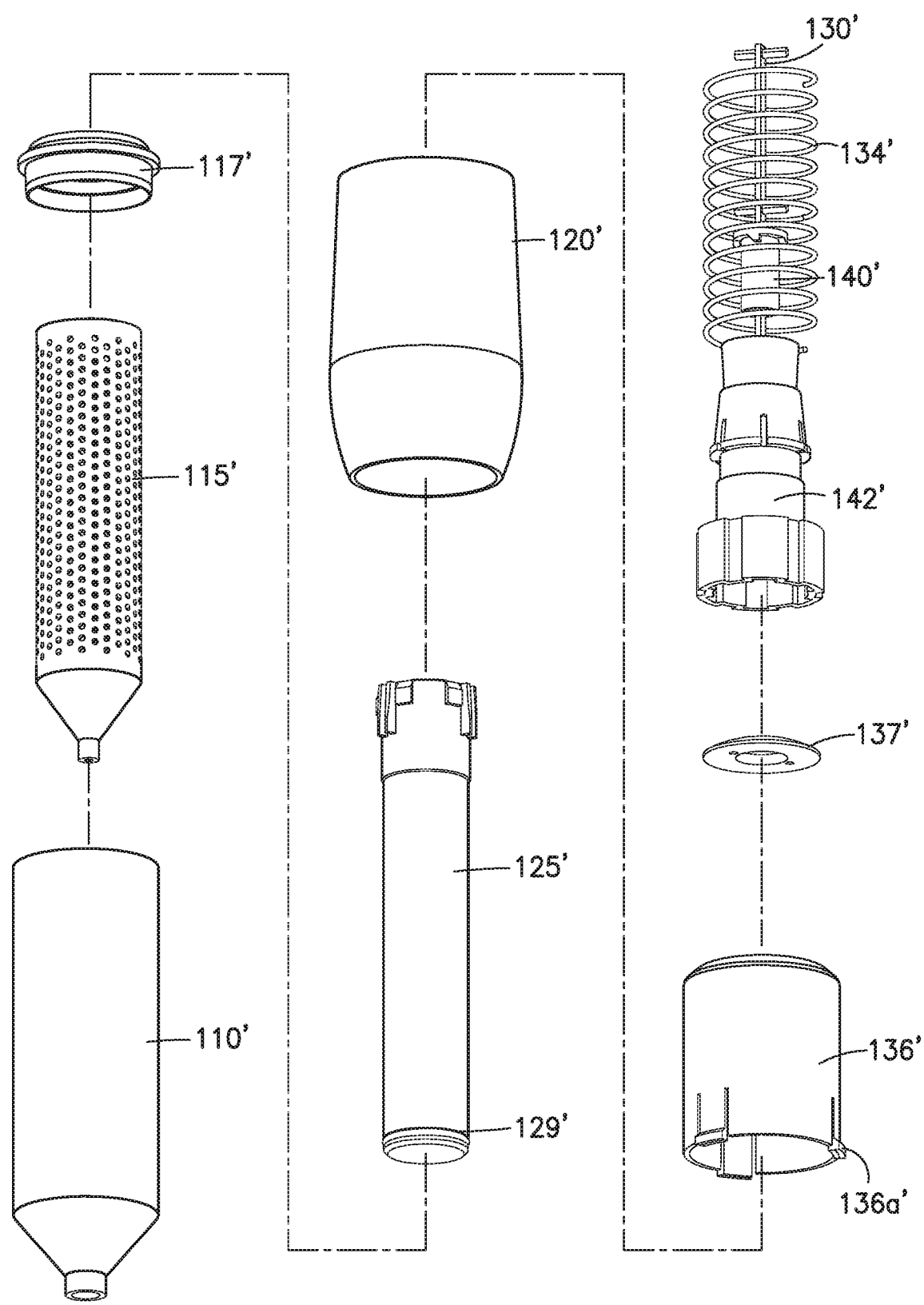

FIGS. 7A and 7B depict a variant of the device of FIGS. 5 and 6, with the size and shape, and orientation of various elements changed. FIG. 7B is an exploded view of the device of FIG. 7A. Referring to FIGS. 7A and 7B, push to spin syringe 100' is depicted, with reference numbers and elements corresponding to the device depicted in FIGS. 5 and 6, omitting reference numbers that are unnecessary to describe the syringe 100'. Functions of elements of syringe 100', unless otherwise described, are essentially as described for syringe 100 of FIGS. 5 and 6. Syringe 100' comprises an external body 110' with a Luer adaptor 111'. A porous inner body 115' is depicted, having a first opening 116a' passing into the lumen of the Luer adaptor 111'. Inner body 115' is retained within the external body 110' by bearings 117'. In all aspects of the syringe, bearings are optional. External plunger body 120' is depicted, as is an internal plunger body 125' with a piston 129', such as a silicone piston for a medical syringe, slidably engaging the inner wall of the inner body 115'. Plunger 130' has helical or spiral threads on its external surface, and is retained in place by plunger retainer 131'. A compression spring 134' is depicted surrounding the plunger 130' and engaging plunger cap 136', which is biased away from the external body 110' by the spring 134' and is slidably retained within the external plunger body 120', e.g., by peripheral barbs 136a' in the cap, engaging a ridge 120a', or other suitable retaining structures formed into the external plunger body 120' and/or the plunger cap 136'. Ratchet 140' is depicted, which engages ratchet retainer 142', which, in turn, engages the internal plunger body 125'. In use, fat is drawn into the inner body 115' by movement of the external plunger body 120' in a direction away from the Luer adapter 111'. Once fat is drawn into the inner body 115', plunger cap 136' is repeatedly pressed in a direction toward the Luer adapter 111' while the user retains the external plunger body 120', causing the plunger 130' to move within and relative to the ratchet 140' to cause the ratchet 140', and, in turn, the ratchet retainer 142', the internal plunger body 125', and, by friction of the piston 129' against the inner surface of the inner body 115', causing the inner body 115' to spin, thereby spinning liquids out from the fat materials drawn into the inner body 115'. Once the spinning is completed, the fat can be injected, e.g., through a needle or cannula, into a desired location in the patient by pressing the plunger cap 136' towards the Luer adaptor 111'.

Figure 8:
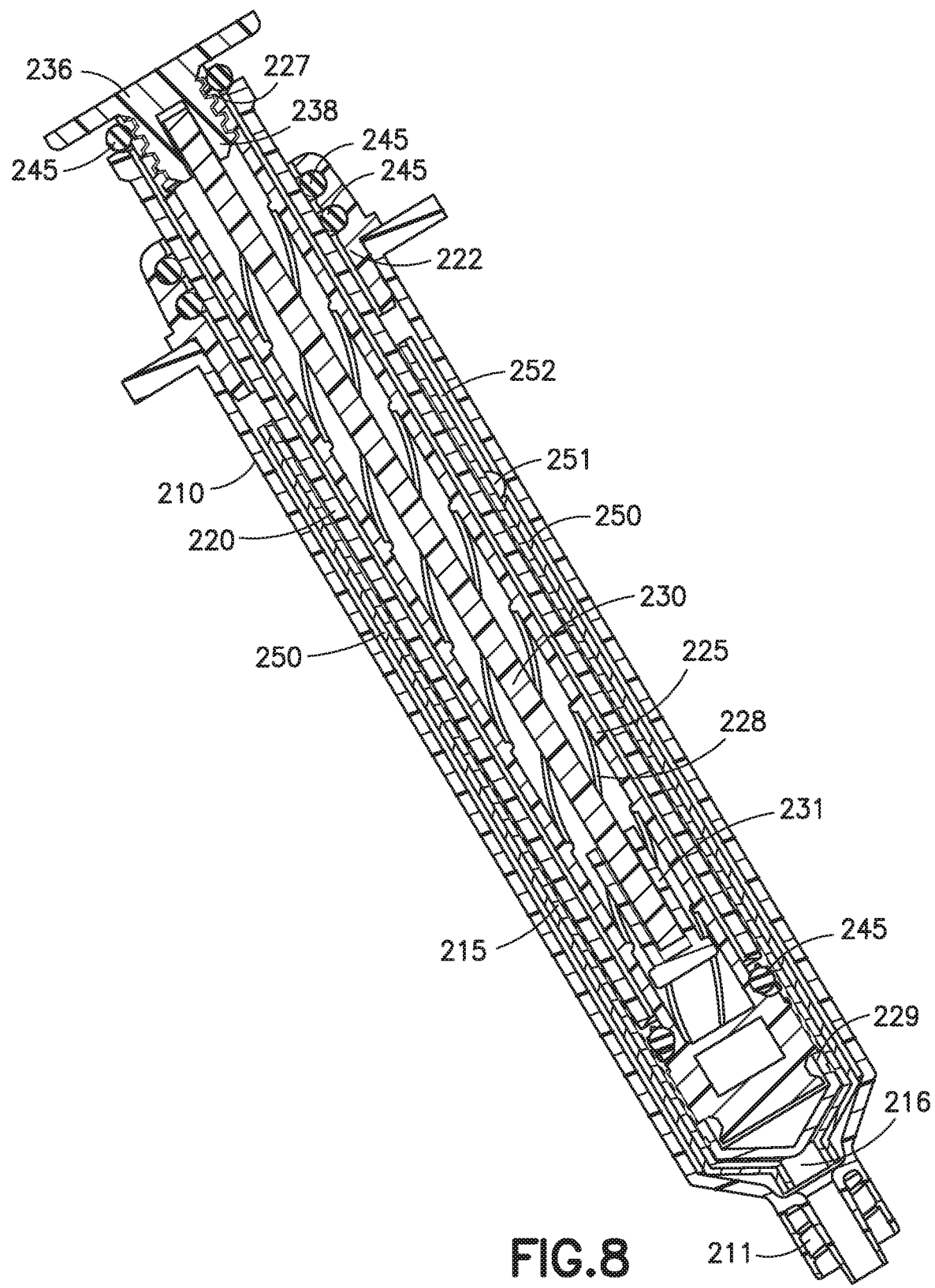
FIG. 8 is a cross-sectional view of one aspect of a fat processing device as described herein.

FIGS. 8 (cross section view) and 9A-9H depict a further aspect of a "push-to-spin" syringe 200, comprising an external body 210 having a Luer adapter 211. As would be recognized to one of ordinary skill, a Luer adaptor is merely exemplary, and any suitable locking or non-locking adaptor may be configured into the device. Disposed inside the external body 210 is an inner body 215 that rotates within the external body 210 and includes a first opening 216. As with inner body 115, described above, the inner body 215 has porous walls. FIG. 9B depicts the inner body, showing a pattern of solid portions 215a, through which liquid cannot pass, and porous portions 215b, through which liquid, but not fat tissue, can pass, e.g., 100 micron (μ) pores. The cross-section of inner body 215 of FIG. 9C shows the even-spacing of the solid portions 215a and porous portions 215b. External plunger body 220 is disposed with the inner portion 115, aligned and sealed within the external body 210 with a plug 222. An internal plunger body 225 is disposed within the external plunger body 220. The internal plunger body 225 has a first end, a threaded portion 227 for receiving a threaded portion of a plunger cap described below, and internal helical or spiral threads 228. Piston 229 is attached to a second end of the internal plunger body 225. A plunger 230 is disposed within the internal plunger body 225, having a ratchet 231 configured to engage the threads 228 of the internal plunger body 228. The ratchet 231 has protuberances configured to engage the spiral threads 228 and a ratchet mechanism, including, for example, a pawl, to permit free rotation of the ratchet 231, while the plunger is pulled in a direction opposite the Luer adaptor 211 and rotation of the ratchet 231 is prevented, e.g., by a pawl, when the plunger is pressed towards the Luer adaptor 211 to spin the inner body 215. A cap 236 with a threaded base 238 is attached to the plunger. The threaded base 238 engages the threaded portion 227 of the internal plunger body 225, and when disengaged (unscrewed) permits the plunger 230 and ratchet 231 to move within the internal plunger body 225, to rotate the internal plunger body 225, and therefore the inner body 215. In practice, it has been determined that no bearings are necessary for this device to function properly. O-rings 245 are provided where needed to seal and/or retain the various elements of the syringe 200.

Figure 9A:
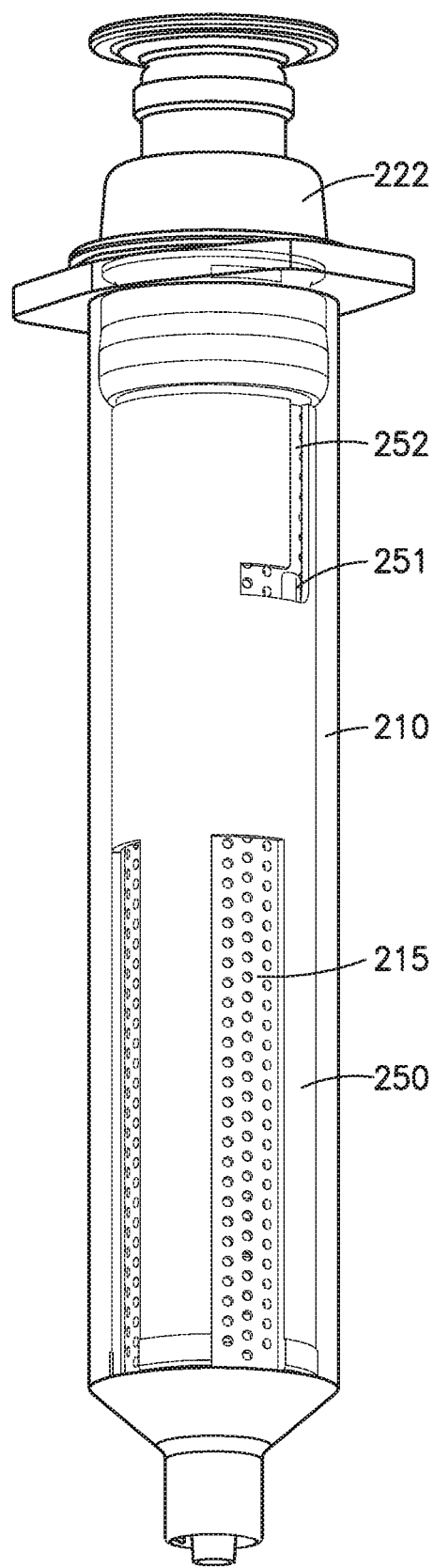
FIG. 9A is an elevation view of the device depicted in FIG. 8.
Figure 9B:
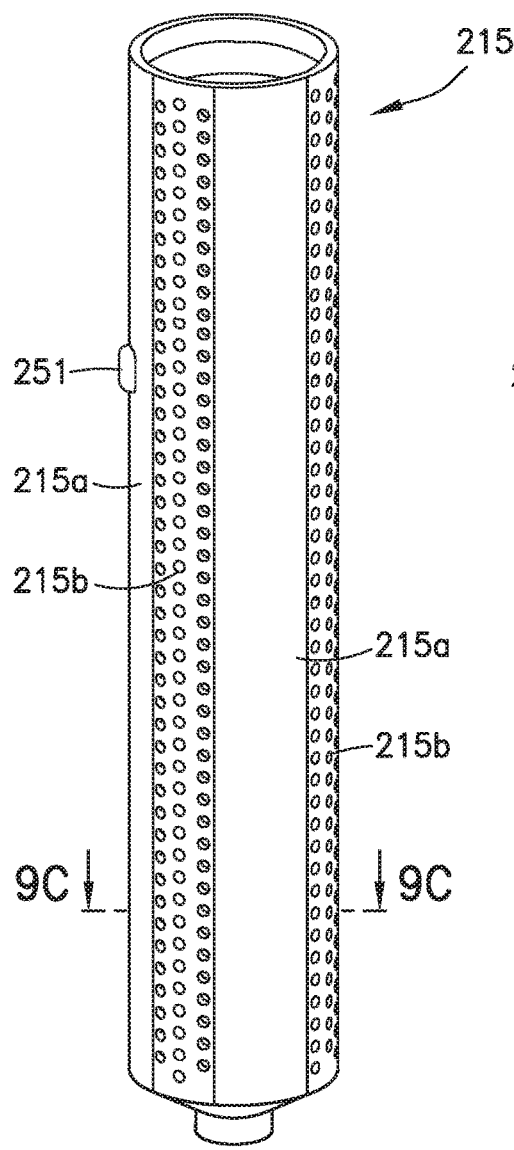
FIGS. 9B-9H are various views of elements of the device depicted in FIGS. 8 and 9A.
Figure 9C:
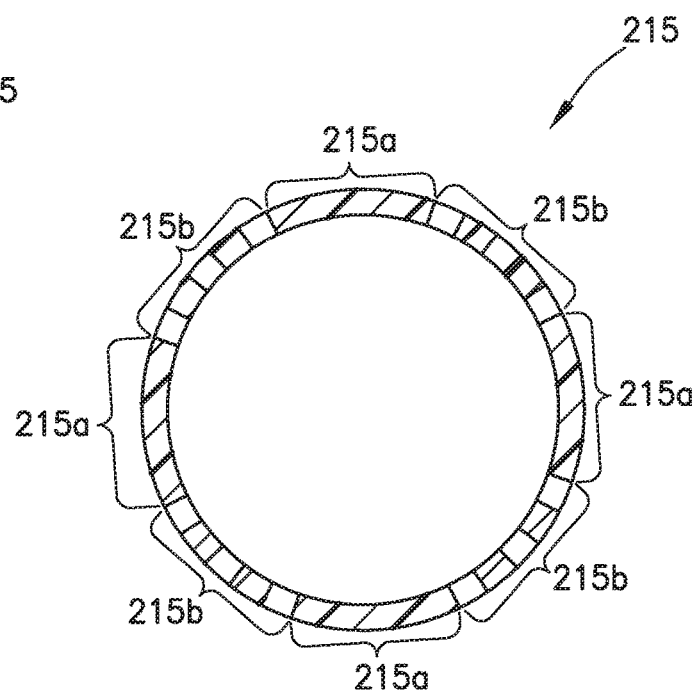
Figure 9D:
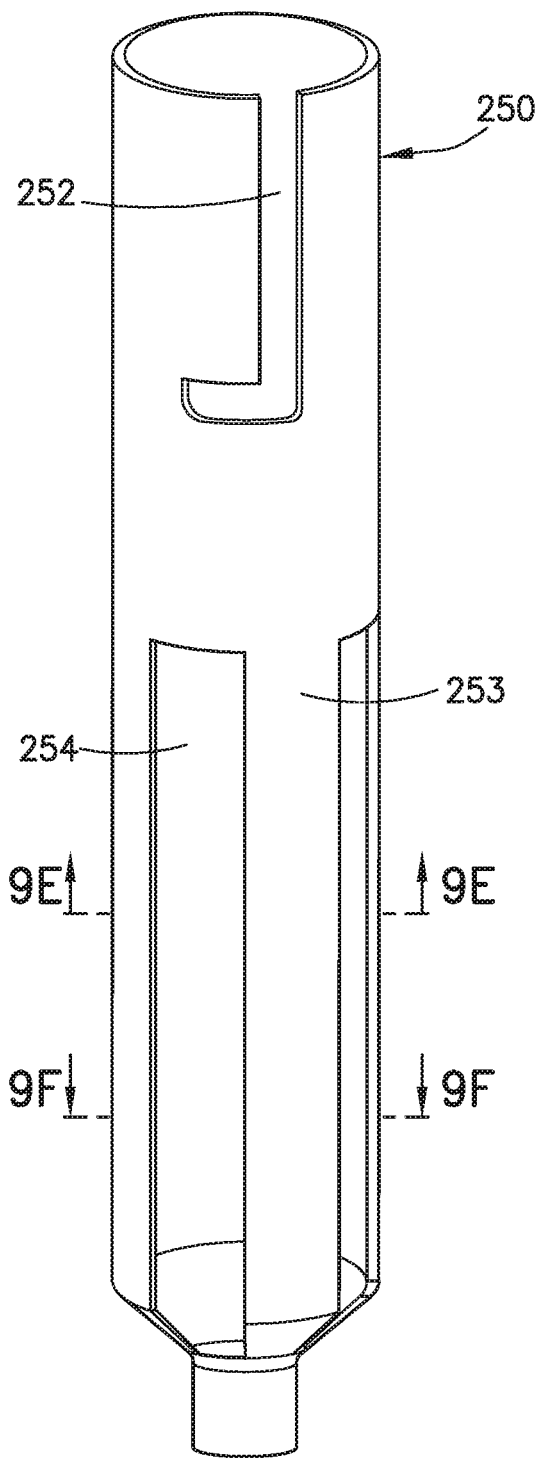
Figure 9F:
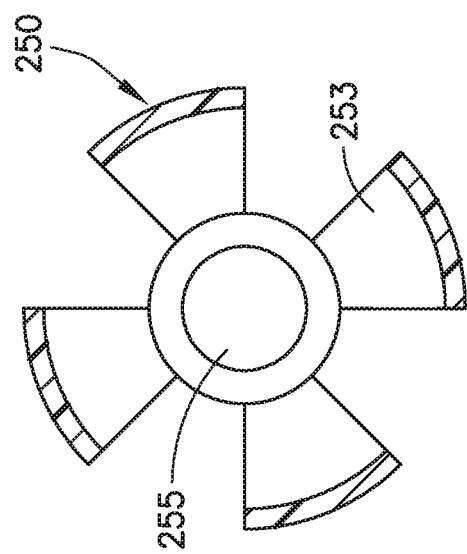
Figure 9E:
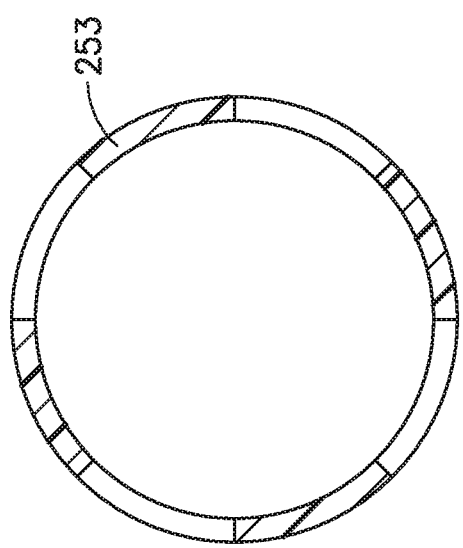
Figure 9H:
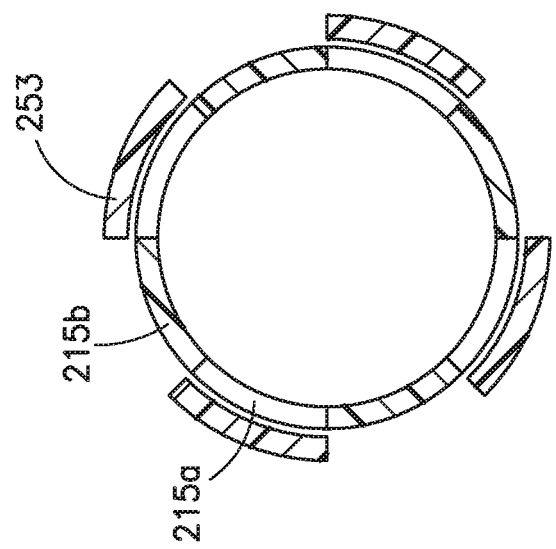
Figure 9G:
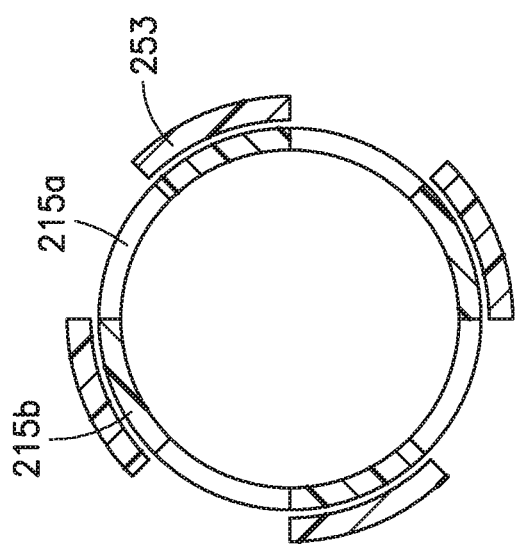

In further reference to FIGS. 8 and 9A-9H, and applicable to any push-to-spin syringe described herein, the pore size of the pores of the inner body 115, 215, etc., may be too large to permit generation of adequate suction while fat tissue is being collected, or cause the fat tissue to eject through the pores when the fat tissue is being delivered. In such a case, it may be desirable to block the pores of the inner body 115, 215, etc. To this end a shield 250 is provided. The shield 250 has an inner surface that contacts the outer surface of the inner body 215. As seen in FIGS. 8 and 9B, the inner body includes a protuberance 251, and as seen in FIGS. 9D-9F the shield 250 includes an L-shaped track 252 into which protuberance 251 extends. Cover portions 253 and gaps 254 are shown, which align with solid portions 215a and porous portions 215b of the inner body. As seen in FIGS. 8 and 9F, the shield 250 includes an opening 255 through which the first opening 216 of the inner body 215 passes. In use, the shield 250 has two positions relative to the inner body 215. In FIG. 9G, the cover portions 253 align with and effectively seal the porous portions 215b of the inner body 215. In FIG. 9H, the cover portions 253 align with the solid portions 215a of the inner body 215. In use, to increase suction during aspiration of fat from the patient and to prevent passage of cells and tissue through the pores during delivery of the fat tissue to a patient, the shield 250 is turned to cover the porous portions 215b of the inner body. When the inner body 215 is spun to remove liquids from the aspirated fat tissue, the shield 250 is turned to open up the porous portions 215b as shown in FIG. 9H. In the device of FIGS. 8 and 9A-9H, the cap 222, and therefore the internal elements of the syringe 200, are removed from the external body 210 in order to turn the shield 250 relative to the inner body 215. Other mechanisms, such as an internal catch or a lever extending externally from the device, can be used to rotate the shield 250 relative to the inner body 215. Other configurations of the shield 250 and porous portions 215b of the inner body 215 can be used, so long as the overall function of the device is not impaired, that is, the ability to draw fat into the inner body 215, spin the inner body 215 so that liquids pass outside the inner body 215, and inject fat cells or tissue from the inner body 215 through a cannula. For example, the shield 250 may only have one cover portion 253 and the inner body 215 would have only one porous portion 215b. Likewise, the shield 250 may have one, two, three, four, five, six, or more cover portion 253 and the internal body 215 would have one, two, three, four, five, six, or more porous portions 215b, respectively.

FIG. 9A depicts the track 252 and protuberance 251 being inside the external body 210, in which case, to move the shield 250, relative to the internal body 215, the shield 250 and elements contained within are removed from the external body 210 by pulling the cap 222. The position of the shield 250 relative to the internal body 215 can then be easily changed by hand, and the shield 250 and elements contained within are then re-inserted into the external body. In another aspect, not shown, a button can be included within and through the wall of the external body, which is biased in an outward direction so as to not contact the shield 250 unless pressed. This would allow rotation of the shield 250 relative to the internal body 215, and when not pressed, the button does not interfere with the action of the device. Alternately, the button may be attached to the shield 250, and passes through the wall of the external body 210 through a slot or hole that is optionally sealed to prevent escape of fluids. In this case, the external body 210 rotates with the internal body 215 and shield 250. Placement of the device in a stand similar to the stand 150 shown in FIG. 5, would allow rotation of the entire syringe device, when the "push-to-spin" mechanism is activated. As would be recognized by one of ordinary skill, these variations to the structure of the syringe 200, including inclusion of a shield and the various methods of rotating the shield relative to the internal body, can be applied to any aspect of the syringe device described herein, e.g., syringe device 100, 100', 200, and 300, as shown in FIGS. 5-10B. Further, the variations to the structure of the syringe 200, including inclusion of a shield and the various methods of rotating the shield relative to the internal body, are merely exemplary of mechanisms for rotationally adjusting the orientation of the shield relative to the internal body.

Figure 10A:
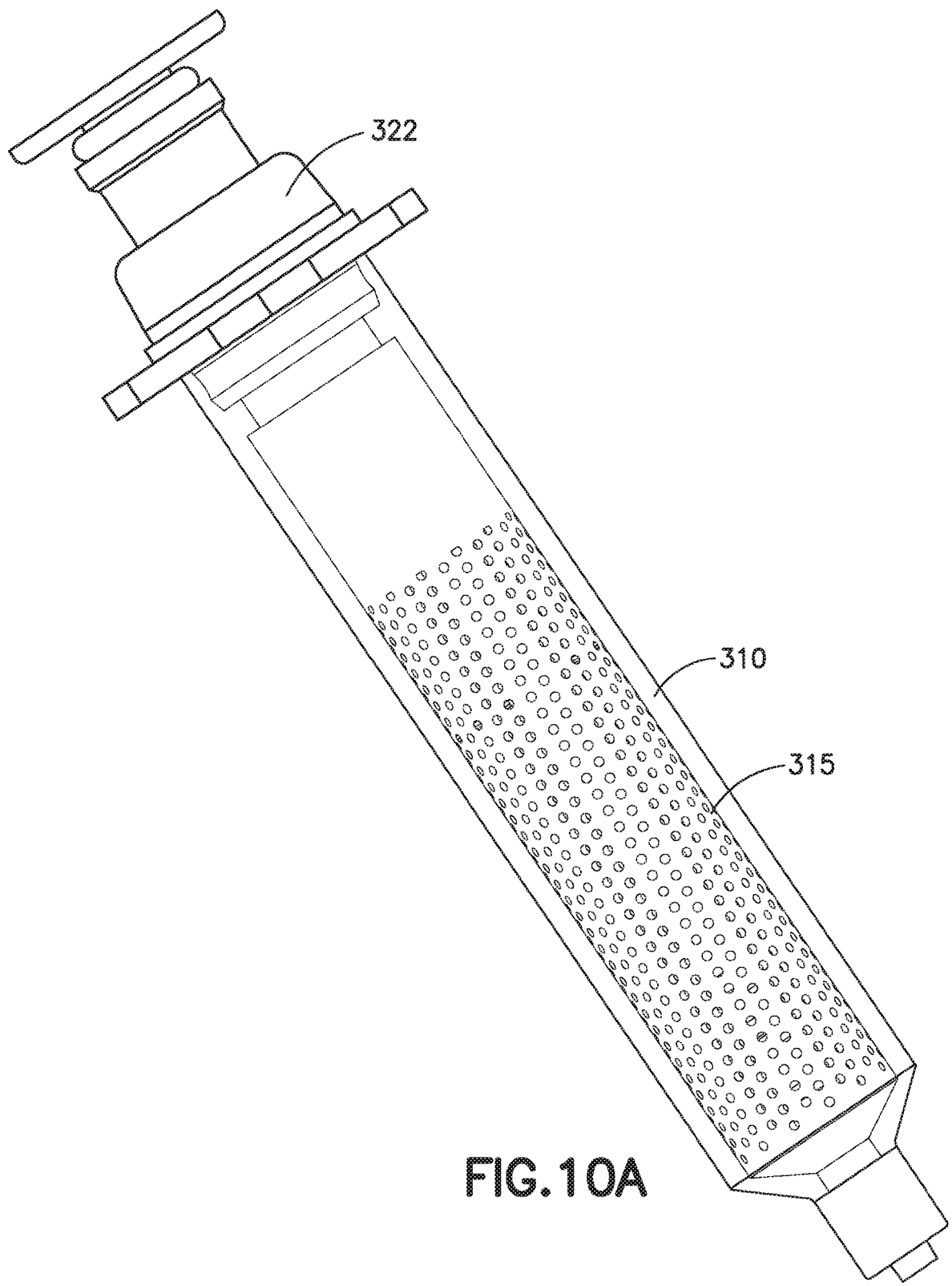
FIGS. 10A and 10B are an elevation and an exploded view of one aspect of a fat processing device as described herein.
Figure 10B:
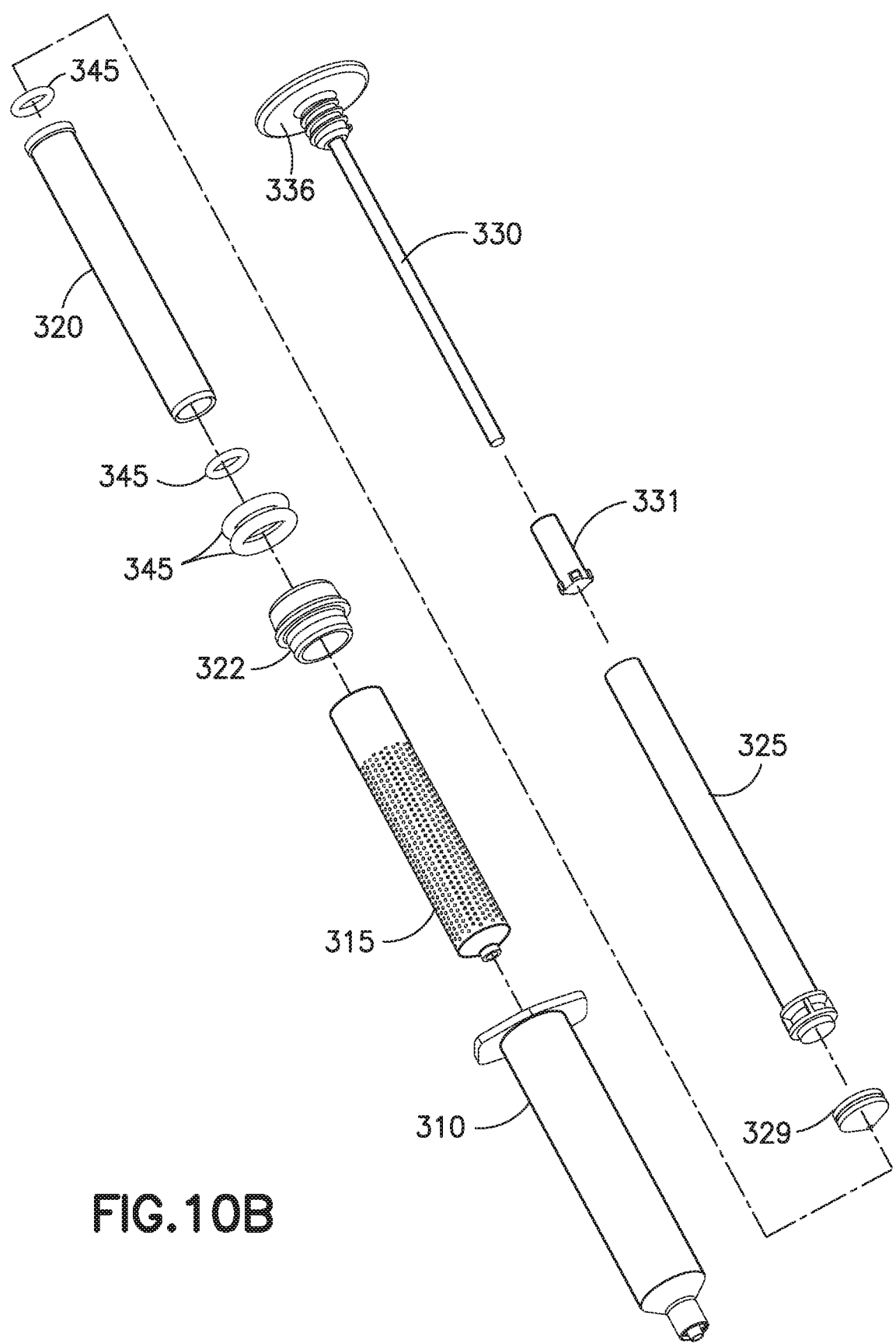

In yet another aspect, referring to FIGS. 10A and 10B (exploded view) a "push-to-spin" syringe 300 is provided, identical to the syringe of FIGS. 8 and 9A-9H, except that no shield 250 is depicted. The syringe 300 comprises an external body 310, an inner body 315, an external plunger body 320, a plug 222, an internal plunger body 225, a piston 329, a plunger 330, a guide 331, a cap 236, and O-rings 245 are depicted. In aspects, the pore size of the inner portion is sufficiently small to afford sufficient suction to aspirate fat tissue and to prevent passage of significant amounts of cellular material though the pores of the inner body 215 during injection of fat cells from the syringe 330.

Of note, although a ratchet is depicted or described in the context of the syringes 100, 100', 200, and 300, permitting spinning of the inner body in one direction only, the ratcheting capability of the structure may be omitted in favor of engagement in both directions of spin, such that moving the plunger in one direction results in spinning in a first direction, and moving the plunger in an opposite direction results in spinning in an opposite direction. Further, it is noted that the structures depicted are merely illustrative and can be optimized, for example and without limitation, functional, ergonomic, or aesthetic purposes. For example, the device can be designed so that the external body rotates with the internal body and, where present, the shield. In such a case, the internal body and external body are physically connected, and can be a unitary structure, formed, for example, by 3D printing, or joined by, e.g., chemical, solvent, or thermal welding processes. Where the external body rotates, the device 100, 100', 200, or 300, can be placed in a stand, such as stand 150, shown schematically in FIG. 5. The stand may optionally include bearings or other low-friction mechanism or structure in contact with the syringe so as to facilitate free spinning of the device.

The syringes 100, 100', 200, and 300, and their elements, where relevant, such as the external body, the internal body, the shield, and certain elements of the spinning mechanism, e.g., as described herein, are generally cylindrical in shape, though this does not rule out that tapered, frusto-conical, or other shapes may be useful.

In a further aspect, also provided is a method of use of the device exemplified in FIGS. 5 and 6 and as described above, for treatment of plantar fasciitis. The method comprises obtaining fat tissue or fat cells from a patient using a syringe 100, 100', 200, or 300, as described above, or an equivalent device, separating the fat tissue or cells from acellular liquids, such as lipids and aqueous liquids using that device, and injecting cells into plantar fascia site of a patient having plantar fasciitis.

In yet another aspect, a method of treating plantar fasciitis is provided. The method comprises injecting an amount of live fat cells into a patient's plantar fascia effective to treat plantar fasciitis in a patient. The cells may be, and are typically autologous. Multiple injections are typically given into the patient's plantar fascia, for example, at a site of inflammation, pain, or thickening of the plantar fascia. Multiple series of injections may be performed on separate days. Any suitable method for injecting the fat cells may be used. Cells may be obtained and delivered using the above-described "push-to-spin" syringe according to any aspect provided herein, and the location of the injections may be ascertained using the guide device according to any aspect provided herein.

Example 1

Sample Plantar Fasciitis Treatment Protocol

Perforating Fat Injections for Plantar Fasciitis and Fasciosis
1. The correct patient is identified by history and physical examination
2. Ultrasound is performed to assess thickness of plantar fascia (usually greater than 4 mm)
3. The location of the plantar fascia for injection is identified (a novel device can be invented to aid in the identification of plantar fascia)
4. The location is verified by palpation and response of pain by the patient
5. The donor sites for fat harvest are identified and injected first with 1% lidocaine and epinephrine at the injection site.
6. 60-120 cc of tumescence is injected with a blunt cannula
7. After waiting the appropriate amount of time (15 min) the fat is harvested using extraction cannulas.
8. The fat is then inserted into the centrifuge at 3000 rpm for 3 minutes
9. The oil layer is wicked off and the aqueous layer is drained
10. The fat is then injected from 10 cc syringes into 1 cc syringes
11. The foot is numbed using local anesthetic
12. A single site in the prior identified zone of injection over the medial band of the plantar fascia is identified
13. The great toe is flexed along with the foot to ensure maximal tension on the fascia for the perforations (a specific device can be created for this and possibly used as a post-operative splint)
14. The fat is then injected through a single site into the plantar fascia using an injection perforation technique. This involves using a blunt cannula
15. The fascia is felt by a resistance or pop and the cannula is passed through the fascia. Fat is injected in each perforation as the cannula is extracted. Several passes are performed less than a mm apart (currently we have ranged from 10-30 but may require many more along the entire length of the fascia) until no resistance is felt. The result is a meshed pattern of fat droplets within the plantar fascia.
16. A single fat preparation device could be employed for Steps 5-12, 14-15, such as the push-to-spin device described above.
17. A post-operative ultrasound is performed to assess thickness of the plantar fascia
18. Post-operative care includes use of a post-operative extension splint or night splint. A special post-op sock or shoe that promotes decreasing pressure on the foot where necessary can be developed for this procedure, as well as other fat grafting procedures
19. Post-operative stretching is encouraged

Example 2

Clinical Results

Fat grafting is a cosmetic and reconstructive procedure that is used sometimes to help improve one's soft tissue thickness, shape and integrity. Autologous fat transplantation is a procedure using a patient's own fat that is taken by a small liposuction tube, from areas with a substantial amount of fat (i.e., abdomen or thighs) and then transferred to another site in the patient, in this case, fibrotic plantar fascia. Perforations are created in the plantar fascia and fat is injected to mesh the plantar fascia, thereby expanding it, and at the same time adding fat for its regenerative properties. Preliminary results suggest this will be successful for treatment of acute or recurrent plantar fasciitis.

This is a minimally invasive incisionless single or multiple site injection technique that can reduce patient downtime and increase physical activity with a reduction in pain. It is a low cost, outpatient procedure that can be performed in an office. Current treatments for chronic plantar fasciitis include extra corporeal shock wave therapy (ultrasound), platelet rich plasma injections, open plantar fasciotomy, endoscopic plantar fasciotomy, and other invasive procedures. Satisfaction with these techniques range from 50-95%, but complications from surgical release of the plantar fascia can include a long recovery, nerve damage and numbness, wound infection, deep vein thrombosis from immobilization, calcaneal cuboid syndrome (lateral foot pain), metatarsal stress fractures, scar formation, and recurrent plantar fasciitis.

This method of perforating the thickened, degenerated tissue in combination with autologous fat infiltration of the plantar fascia may repair it and improve flexibility. Fat contains adipose derived stem cells and it is thought that the fat itself has the ability to stimulate a regenerative healing process rather than one of scar and inflammation. Ideally the regenerative properties of the fat graft will repair and improve the integrity of the plantar fascia while minimizing scar formation and the heel pain will subside.

This is being studied in a randomized crossover clinical trial of twenty patients. To date, one of the study participants, presented with a 3 year history of left heel pain which was progressively getting worse. She reported sharp pain at her left heel with her first steps out of bed, every time she got up from a seated position, and throbbing pain by the end of the day. She failed conservative treatment including cortisone injections, physical therapy, orthotic management and use of a night splint. At her initial screen the ultrasound measurement of her left foot plantar fascia was 0.56 cm thickness. The asymptomatic right foot plantar fascia measured 0.3 cm thickness. She randomized into the standard of care group and tried using night splints and supportive straps for six months. She noted increased discomfort after the 6 months of conservative care.

After 6 months, she underwent fat injections into the plantar fascia. Fat was harvested from her abdomen under local anesthesia. The fat was processed in a standard fashion and 3 ml were injected into the left foot through a single injection site under local anesthesia. At her one month post operative visit her pain had returned to baseline and her ultrasound plantar fascia thickness measurement was 0.49 cm. She was advised to aggressively stretch her foot with the night splint for the next month. At 2 months, she reported an increased number of "good days" with improved pain. On ultrasound her plantar fascia averaged thickness measurement was 0.29 cm. She was advised to continue to aggressively stretch her foot and return to more normal activity with reevaluation in 4 months (6 months post op).

Improvement is noted with fat grafting for chronic plantar fasciitis. The procedure and treatment protocol are being modified with increased injection sites, increased adipose infiltrate, and more aggressive post op stretching. Greater improvements are observed with these changes.

Example 3

INTRODUCTION: Plantar fasciitis (PF) is the most common cause of heel pain, and chronic PF is a painful condition resulting from recurrent inflammation and degeneration of the plantar fascia insertion at the calcaneal tuberosity. Fascial thickening can cause tremendous pain and reduce quality of life. Current treatment options can be invasive, with complication risks, or non-invasive with inconsistent results. We evaluated a novel method of perforating fat injections to regenerate the plantar fascia and reduce pain and improve quality of life.

METHODS: We report a prospective, randomized crossover pilot study. Included patients had chronic PF with thickening (>4 mm) and failed standard treatment for 6 months. Subjects were randomized to either observation or intervention groups. Intervention involved perforating autologous fat injections to the PF at multiple sites. Subjects were evaluated at baseline, 1-/2-/6-months. Outcomes included validated foot pain and function questionnaires, plantar fascia thickness, and physical exam. Unpaired t-test was used ($p<0.05$).

RESULTS: 15 human subjects were enrolled and randomized (14 female; mean age 49.9±12.4 years, mean BMI 29.1±4.8; observation, n=6; intervention, n=9) following a diagnosis of chronic PF for >4 years. Mean injection volume was 2.6±1.6 cc/foot. At baseline, there were no significant differences between the groups. Six and 12 months after intervention, experimental group had significantly less thick plantar fascia measured by ultrasound ($p<0.05$), while the observational group displayed no change in plantar fascia thickness ($p>0.05$). The experimental group had improvements in pain at 1, 2, 6, and 12 months post-operative ($p<0.05$) while the observational group reported the same pain levels compared to pre-op at 1 and 2 months ($p>0.05$), then improvement at 6 months after the procedure ($p=0.03$). Both groups reported improved functionality following the procedure ($p<0.05$). No unanticipated complications occurred.

CONCLUSION: Perforating fat injections to the plantar fascia demonstrate promising improvements in pain and daily activities. Autologous fat grafting proves to have a regenerative potential in remodeling chronically thickened plantar fascia and eliminating pain.

The following numbered clauses describe exemplary aspects of the invention.

1. A fat grafting device, comprising:
   a rotatable internal body having a lumen, an axis of rotation, a first end comprising a central outlet from the lumen, a porous wall configured to retain fat tissue or cells within the lumen and pass liquids through the wall, and a second end opposite the first end, having an opening;
   an external body surrounding and rotatably retaining the internal body, the external body having a first end comprising a cannula adaptor, such as a Luer adaptor, aligned with and optionally surrounding at least a portion of the central outlet of the internal body, and a second end opposite the first end, having an opening;
   a piston slidably disposed within the internal body and having a peripheral seal engaging an inner surface of the porous wall of the internal body;
   an internal plunger body attached to the piston and defining a central cavity;
   an external plunger body rotatably retaining the internal plunger body and disposed at the second end of the external body; and
   a drive assembly attached to the internal plunger body and comprising within the internal plunger body, either:
   a cylindrical plunger having spiral threads, a ratchet configured to engage the spiral threads of the plunger, and a retainer attached to the internal plunger body configured to engage the ratchet, or
   spiral threads on an inside surface of the internal plunger body, a plunger, and a ratchet affixed to the plunger so as to rotate in only one direction, the ratchet engaging the spiral threads on the inside surface of the internal plunger body,
   wherein the piston engages the internal body, so that when the internal plunger body and piston is rotated, the internal body rotates.

2. The device of clause 1, wherein the drive assembly comprises a cylindrical plunger having spiral threads, a ratchet configured to engage the spiral threads of the plunger, and a retainer attached to the internal plunger body configured to engage the ratchet.

3. The device of clause 2, wherein the retainer only engages the ratchet when the ratchet is rotated in one direction.

4. The device of clause 3, wherein the ratchet and retainer engage and thereby rotate the internal plunger body in a first direction when the cylindrical plunger is moved axially in a direction towards the external body and disengage when the cylindrical plunger is moved axially in a direction away from the external body.

5. The device of clause 1, wherein the drive assembly comprises a plunger, and a ratchet affixed to the plunger and configured to rotate in one direction and engaging spiral threads on an inside surface of the internal plunger body.

6. The device of any one of clauses 1-5, further comprising a compression spring biasing the plunger in a direction opposite the central cannula adaptor.

7. The device of any one of clauses 1-6, wherein the external body further comprises a drain outlet.

8. The device of any one of clauses 1-7, the wall of the internal body having an outer surface, and comprising a pattern of one or more porous areas and one or more non-porous areas, the device further comprising a movable shield external to and contacting the outer surface of the wall of the internal body, wherein the shield is configured to move from a closed position, that blocks the one or more porous areas of the internal body, thereby restricting passage of air into the internal body through the pores during aspiration of fat through a cannula attached to the cannula adaptor, and restricting passage of cells through the pores during fat injection through a cannula attached to the cannula adaptor, to an open position that permits passage of liquid through the one or more porous areas when the internal body is spun.

9. The device of clause 8, wherein the wall of the internal body comprises two, three, four, five, or six evenly-spaced porous areas that extend axially along the wall of the internal body, and the shield comprises an equal number of shield portions separated by gaps, aligning with and being the same size or larger than the porous areas of the internal body, and covering the porous areas in a first rotation position about the internal body, and uncovering the porous areas in a second rotation position about the internal body.

10. A guide device adapted to a human foot, for use in identifying one or more plantar fascia landmarks, comprising:
- a support member, comprising:
  - a curved first portion adapted to or configured to receive a posterior surface of a heel, for example with a major surface on the inside of the curve, and having a lateral and a medial end;
  - a second portion connected to and extending in an anterior direction from the medial end of the first portion, optionally having a major surface facing laterally or adapted to or configured to a medial side of a foot extending from the heel to the arch of the foot;
  - a third portion connected to and extending from an anterior end of the second portion, adapted to or configured to the arch of a foot, e.g. comprising a twist in which the major surface of the support member rotates from facing in a lateral direction towards a side of the foot to facing in a superior direction towards the plantar surface of the foot; and
  - a fourth portion connected to an end of the third portion opposite the second portion and extending towards toes of a foot, in an anterior direction from the third portion and optionally having a first major surface adapted to or configured to face a plantar surface of a foot, e.g. facing in a superior;
- a heel guide adapted to or configured to cross a plantar surface of a heel, e.g., extending laterally from an inferior side of the first or second portion of the support member, and optionally wherein the heel guide is arcuate with an anterior concave side; and
- a guide member strip having a first end attached to the heel guide and a second end fastened to the fourth portion of the support member and defining a guide opening adapted to or configured to center over a landmark of the plantar fascia when the guide member is aligned over the planter fascia, optionally, with the guide member strip passing over the distal metatarsal head and calcaneus bone, wherein the landmark is an injection site on the plantar fascia, for example, an injection site for a corticosteroid, PRP (platelet-rich plasma), SVF (stromal vascular fraction), or fat cells or tissue.

11. The device of clause 10, wherein the guide member strip is reversibly fastened with a fastener, such as a screw, pin, or clamp, to the heel guide and/or the fourth portion of the support member so that the orientation of the guide member strip is adjustable, e.g., can be aligned to an individual patient's plantar fascia.

12. The device of clause 11, wherein the heel guide and/or the fourth portion of the support member comprises holes or slots adapted to reversibly engage one of the fasteners.

13. The device of any one of clauses 10-12, wherein the support member further includes a medial injection guide configured to guide medial injection into the plantar fascia.

14. A method of separating live fat cells and tissue from liquids, comprising:
- drawing live fat cells or fat tissue into the internal body of the device of any one of clauses 1-9 by moving the piston axially away from the first end of the external body;
- rotating the internal body of the device by moving the cylindrical plunger in an axial direction relative to the ratchet, thereby rotating the ratchet; and
- ejecting the fat cells or tissue from the internal body by moving the piston axially toward the first end of the external body.

15. A method of grafting live fat cells and tissue in a patient, comprising:
- drawing live fat cells or fat tissue through a cannula and into the internal body of the device of any one of clauses 1-9 by moving the piston axially away from the first end of the external body;
- rotating the internal body of the device by moving the cylindrical plunger in an axial direction relative to the ratchet, thereby rotating the ratchet; and injecting the fat cells or tissue from the internal body by moving the piston axially toward the first end of the external body.

16. The method of clause 10, wherein the patient has plantar fasciitis in a plantar fascia, and the fat cells are injected a plurality of times into the plantar fascia, e.g., in a pattern along the plantar fascia, thereby improving one or more symptom of plantar fasciitis in the patient, such as reducing pain, reducing inflammation of the plantar fascia, or reducing thickness of the plantar fascia.

17. The method of clause 11, further comprising, fitting the guide device of any one of clauses 10-13 to a foot of the patient prior to injecting the fat cells or tissue, and guiding injection of the fat cells or tissue into the plantar fascia with a guide opening of the guide member strip.

18. The method of clause 17, comprising drawing an outline of a guide opening of the guide member strip on the foot and removing the guide device from the foot prior to injection of the fat cells or fat tissue.

19. The method of any one of clauses 15-18, wherein the fat cells or fat tissue are autologous to the patient into which the fat cells or fat tissue are injected.

20. A method of treating plantar fasciitis in a patient, comprising injecting fat cells into the plantar fascia of the patient in an amount effective to treat plantar fasciitis in a patient.

21. The method of clause 20, wherein the injection of fat cells reduce inflammation, pain, or plantar fascia thickness associated with plantar fasciitis in the patient.

22. The method of clause 20, wherein the fat cells are injected at more than one location in a plantar fascia of a patient.

23. The method of clause 20, wherein the injection of fat cells is repeated on different days.

The embodiments have been described with reference to various examples. Modifications and alterations will occur to others upon reading and understanding the foregoing examples. Accordingly, the foregoing examples are not to be construed as limiting the disclosure.

We claim:

1. A fat grafting device, comprising:
- a rotatable internal body having a lumen, an axis of rotation, a first end comprising a central outlet from the lumen, a porous wall configured to retain fat tissue or cells within the lumen and pass liquids through the wall, and a second end opposite the first end, having an opening;
- an external body surrounding and rotatably retaining the internal body, the external body having a first end comprising a cannula adaptor aligned with at least a portion of the central outlet of the internal body, and a second end opposite the first end, having an opening;

a piston slidably disposed within the internal body and having a peripheral seal engaging an inner surface of the porous wall of the internal body;

an internal plunger body attached to the piston and defining a central cavity;

an external plunger body rotatably retaining the internal plunger body and disposed at the second end of the external body; and a drive assembly attached to the internal plunger body and comprising within the internal plunger body, either:

a cylindrical first plunger having first spiral threads, a first ratchet configured to engage the first spiral threads of the cylindrical first plunger, and a retainer attached to the internal plunger body configured to engage the first ratchet, or second spiral threads on an inside surface of the internal plunger body, a second plunger, and a second ratchet affixed to the second plunger so as to rotate in only one direction, the second ratchet engaging the second spiral threads on the inside surface of the internal plunger body, wherein the piston engages the internal body, so that when the internal plunger body and piston are rotated, the internal body rotates.

2. The device of claim 1, wherein the drive assembly comprises the cylindrical first plunger having the first spiral threads, the first ratchet configured to engage the first spiral threads of the cylindrical first plunger, and the retainer attached to the internal plunger body configured to engage the first ratchet.

3. The device of claim 2, wherein the retainer only engages the first ratchet when the first ratchet is rotated in one direction.

4. The device of claim 3, wherein the first ratchet and the retainer engage and thereby rotate the internal plunger body in a first direction when the cylindrical first plunger is moved axially in a direction towards the external body and disengage when the cylindrical first plunger is moved axially in a direction away from the external body.

5. The device of claim 1, wherein the drive assembly comprises the second plunger, and the second ratchet affixed to the second plunger and configured to rotate in one direction and engaging the second spiral threads on the inside surface of the internal plunger body.

6. The device claim 5, further comprising a compression spring biasing the second plunger in a direction opposite the cannula adaptor.

7. The device of claim 1, wherein the external body further comprises a drain outlet.

8. The device of claim 1, the wall of the internal body having an outer surface, and comprising a pattern of one or more porous areas and one or more non-porous areas, the device further comprising a movable shield external to and contacting the outer surface of the wall of the internal body, wherein the shield is configured to move from a closed position, that blocks the one or more porous areas of the internal body, thereby restricting passage of air into the internal body through the pores during aspiration of fat through a cannula attached to the cannula adaptor, and restricting passage of cells through the pores during fat injection through the cannula attached to the cannula adaptor, to an open position that permits passage of liquid through the one or more porous areas when the internal body is spun.

9. The device of claim 8, wherein the wall of the internal body comprises two, three, four, five, or six evenly-spaced porous areas that extend axially along the wall of the internal body, and the shield comprises a number of shield portions equal to a number of the evenly-spaced porous areas separated by gaps, aligning with and being the same size or larger than the porous areas of the internal body, and covering the porous areas when the shield is in the closed position, and uncovering the porous areas when the shield is in the open position.

10. A method of separating live fat cells and tissue from liquids, comprising:

drawing live fat cells or fat tissue into the internal body of the device of claim 1 by moving the piston axially away from the first end of the external body;

rotating the internal body of the device by moving the cylindrical first plunger in an axial direction relative to the first ratchet, thereby rotating the first ratchet; and ejecting the fat cells or tissue from the internal body by moving the piston axially toward the first end of the external body.

11. The device of claim 1, wherein the cannula adaptor of the first end of the external body comprises a Luer adaptor.

12. The device of claim 1, wherein the cannula adaptor surrounds at least a portion of the central outlet of the internal body.

13. A method of grafting live fat cells and tissue in a patient, comprising:

drawing live fat cells or fat tissue through a cannula and into the internal body of the device of claim 1 by moving the piston axially away from the first end of the external body;

rotating the internal body of the device by moving the cylindrical first plunger in an axial direction relative to the first ratchet, thereby rotating the first ratchet; and injecting the fat cells or tissue from the internal body by moving the piston axially toward the first end of the external body.

14. The method of claim 13, wherein the fat cells or tissue is injected into a plantar fascia of a patient with plantar fasciitis, and wherein the fat cells are injected a plurality of times into the plantar fascia, thereby improving one or more symptom of plantar fasciitis in the patient.

15. The method of claim 14, further comprising, fitting a guide device to a foot of the patient prior to injecting the fat cells or tissue, and guiding injection of the fat cells or tissue into the plantar fascia with a guide opening of the guide member strip, the guide device comprising:

a support member, comprising:

a curved first portion adapted to or configured to receive a posterior surface of a heel and having a lateral and a medial end;

a second portion connected to and extending in an anterior direction from the medial end of the first portion facing laterally or adapted to or configured to a medial side of the foot extending from the heel to an arch of the foot;

a third portion connected to and extending from an anterior end of the second portion, adapted to or configured to the arch of the foot; and a fourth portion connected to an end of the third portion opposite the second portion and extending towards toes of the foot, in an anterior direction from the third portion adapted to or configured to face a plantar surface of the foot;

a heel guide extending from the support member adapted to or configured to cross a plantar surface of the heel; and a guide member strip having a first end attached to the heel guide and a second end fastened to the fourth portion of the support member and defining the guide opening adapted to or configured to center over a landmark of the plantar fascia when the guide member is aligned over the planter fascia, wherein the landmark is an injection site on the plantar fascia.

16. The method of claim 15, comprising drawing an outline of the guide opening of the guide member strip on the foot and removing the guide device from the foot prior to injection of the fat cells or fat tissue.

17. The method of claim 13, wherein the fat cells or fat tissue are autologous to the patient into which the fat cells or fat tissue are injected.

18. The method of claim 14, wherein the fat cells are injected into the plantar fascia in a pattern along the planter fascia.

19. The method of claim 14, wherein the one or more symptoms of plantar fasciitis improved by injection of the fat cells comprises at least one of reducing pain, reducing inflammation of the plantar fascia, or reducing thickness of the plantar fascia.

20. The method of claim 15, wherein the curved first portion of the support member comprises a first major surface on an inside of the curved first portion and the second portion of the support member comprises a second major surface facing laterally or adapted to or configured to the medial side of the foot extending from the heel to the arch of the foot.

21. The method of claim 20, wherein the third portion of the support member comprises a twist in which the second major surface of the second portion of the support member rotates from facing in a lateral direction towards a side of the foot to facing in a superior direction towards the plantar surface of the foot.

22. The method of claim 15, wherein the heel guide is adapted to or configured to extend laterally from an inferior side of the first portion or the second portion of the support member, and wherein the heel guide is arcuate with an anterior concave side.

23. The method of claim 15, wherein the guide member strip is adapted to or configured to pass over a distal metatarsal head and calcaneus bone.

\* \* \* \* \*

UNITED STATES PATENT AND TRADEMARK OFFICE
CERTIFICATE OF CORRECTION

PATENT NO. : 11,918,793 B2
APPLICATION NO. : 16/642568
DATED : March 5, 2024
INVENTOR(S) : Jeffrey Gusenoff et al.

It is certified that error appears in the above-identified patent and that said Letters Patent is hereby corrected as shown below:

In the Claims

Column 23, Line 48, Claim 6, delete "device" and insert -- device of --

Signed and Sealed this
Fourth Day of June, 2024

Katherine Kelly Vidal
*Director of the United States Patent and Trademark Office*